United States Patent
Aznoian et al.

(10) Patent No.: US 8,206,284 B2
(45) Date of Patent: Jun. 26, 2012

(54) INTEGRATED ENDOSCOPE AND ACCESSORY TREATMENT DEVICE

(75) Inventors: Harold M. Aznoian, North Andover, MA (US); Richard L. Costa, Burlington, MA (US); John Dimitriou, Stow, MA (US); Richard A. Gambale, Tyngsboro, MA (US); Peter J. Lukin, Norfolk, MA (US); Edward C. Page, Baldwinville, MA (US); Sean J. Silva, North Reading, MA (US); David T. Zelonis, Pepperell, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 137 days.

(21) Appl. No.: 12/725,283

(22) Filed: Mar. 16, 2010

(65) Prior Publication Data

US 2010/0174140 A1    Jul. 8, 2010

Related U.S. Application Data

(60) Division of application No. 12/072,441, filed on Feb. 26, 2008, now Pat. No. 8,057,386, which is a continuation of application No. 10/658,135, filed on Sep. 8, 2003, now abandoned.

(60) Provisional application No. 60/408,556, filed on Sep. 6, 2002.

(51) Int. Cl.
*A61B 1/00* (2006.01)
(52) U.S. Cl. ......... 600/104; 600/156; 606/139; 606/144
(58) Field of Classification Search .......... 606/139–150; 600/153–159
See application file for complete search history.

(56) References Cited

U.S. PATENT DOCUMENTS

| | | | |
|---|---|---|---|
| 453,508 A | 6/1891 | Ruby |
| 730,152 A | 6/1903 | Pitner |
| 979,342 A | 12/1910 | Schaefer |
| 1,325,699 A | 12/1919 | Oesterhaus |
| 1,868,308 A | 7/1932 | Brumfield |
| 2,170,599 A | 8/1939 | Stricklen |
| 2,587,364 A | 2/1952 | Mitchell |
| 2,601,852 A | 7/1952 | Wendt |
| 2,621,655 A | 12/1952 | Olson |
| 2,650,593 A | 9/1953 | Weil et al. |

(Continued)

FOREIGN PATENT DOCUMENTS

DE    3402910 A1    8/1984

(Continued)

OTHER PUBLICATIONS

Bard Interventional Products Division, C.R. Bard, Inc., "RapidFire™ Multiple Band Ligator—Information for Use", No. AE1904601/01, Issued Jun. 1996.

(Continued)

*Primary Examiner* — Matthew J Kasztejna
(74) *Attorney, Agent, or Firm* — Wolf, Greenfield & Sacks, P.C.

(57) ABSTRACT

An integrated endoscope and accessory treatment device is provided. The device employs a medical treatment device at its distal end that is combined with the endoscope as a complete system. The treatment device is controlled by integrated elements at the proximal end of the endoscope. The treatment devices may include tissue apposition devices, tissue cutting devices, forceps and others.

14 Claims, 21 Drawing Sheets

U.S. PATENT DOCUMENTS

| | | | |
|---|---|---|---|
| 2,880,728 A | 4/1959 | Rights |
| 3,013,559 A | 12/1961 | Thomas |
| 3,168,097 A | 2/1965 | Dormia |
| 3,238,941 A | 3/1966 | Klein et al. |
| 3,470,875 A | 10/1969 | Johnson |
| 3,716,058 A | 2/1973 | Tanner |
| 3,757,781 A | 9/1973 | Smart |
| 3,760,810 A | 9/1973 | Van Hoorn |
| 3,845,772 A | 11/1974 | Smith |
| 3,858,571 A | 1/1975 | Rudolph |
| 4,126,124 A | 11/1978 | Miller |
| 4,144,876 A | 3/1979 | DeLeo |
| 4,164,225 A | 8/1979 | Johnson et al. |
| 4,210,148 A | 7/1980 | Stivala |
| 4,216,777 A | 8/1980 | Pridemore |
| 4,226,239 A | 10/1980 | Polk et al. |
| 4,234,111 A | 11/1980 | Dischinger |
| 4,236,470 A | 12/1980 | Stenson |
| 4,291,698 A | 9/1981 | Fuchs et al. |
| 4,345,601 A | 8/1982 | Funkunda |
| 4,414,908 A | 11/1983 | Eguchi et al. |
| 4,415,092 A | 11/1983 | Boyer |
| 4,440,171 A | 4/1984 | Nomoto et al. |
| 4,469,101 A | 9/1984 | Coleman et al. |
| 4,474,174 A | 10/1984 | Petruzzi |
| 4,493,319 A | 1/1985 | Polk et al. |
| D279,504 S | 7/1985 | Tump |
| 4,557,265 A | 12/1985 | Andersson |
| 4,597,390 A | 7/1986 | Mulhollan et al. |
| 4,607,620 A | 8/1986 | Storz |
| 4,615,472 A | 10/1986 | Nash |
| 4,621,640 A | 11/1986 | Mulhollan et al. |
| 4,637,816 A | 1/1987 | Mann |
| 4,665,906 A | 5/1987 | Jervis |
| 4,672,979 A | 6/1987 | Pohndorf |
| 4,706,653 A | 11/1987 | Yamamoto |
| 4,721,103 A | 1/1988 | Freedland |
| 4,735,194 A | 4/1988 | Stiegmann |
| 4,738,255 A | 4/1988 | Goble et al. |
| 4,741,330 A | 5/1988 | Hayhurst |
| 4,747,358 A * | 5/1988 | Moll et al. ............ 112/169 |
| 4,759,364 A | 7/1988 | Boebel |
| 4,794,911 A | 1/1989 | Okada |
| 4,825,259 A | 4/1989 | Berry, Jr. |
| 4,841,888 A | 6/1989 | Mills et al. |
| 4,860,746 A | 8/1989 | Yoon |
| 4,890,615 A | 1/1990 | Caspari et al. |
| 4,898,156 A | 2/1990 | Gatturna et al. |
| 4,899,743 A | 2/1990 | Nicholson et al. |
| 4,899,746 A | 2/1990 | Brunk |
| 4,923,461 A | 5/1990 | Caspari et al. |
| 4,927,428 A | 5/1990 | Richards |
| 4,932,962 A | 6/1990 | Yoon et al. |
| 4,936,823 A | 6/1990 | Colvin et al. |
| 4,946,468 A | 8/1990 | Li |
| 4,950,285 A | 8/1990 | Wik |
| 4,968,315 A | 11/1990 | Gatturna |
| 5,002,042 A | 3/1991 | Okada |
| 5,002,550 A | 3/1991 | Li |
| 5,037,021 A | 8/1991 | Mills et al. |
| 5,037,422 A | 8/1991 | Hayhurst et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,078,731 A | 1/1992 | Hayhurst |
| 5,080,663 A | 1/1992 | Mills et al. |
| 5,100,417 A | 3/1992 | Cerier et al. |
| 5,100,418 A | 3/1992 | Yoon et al. |
| 5,100,421 A | 3/1992 | Christoudias |
| 5,102,421 A | 4/1992 | Anspach et al. |
| 5,116,349 A | 5/1992 | Aranyi |
| 5,123,913 A | 6/1992 | Wilk et al. |
| 5,125,553 A | 6/1992 | Oddsen et al. |
| 5,147,379 A | 9/1992 | Sabbaghian et al. |
| 5,152,769 A | 10/1992 | Baber |
| 5,163,945 A | 11/1992 | Ortiz et al. |
| 5,171,251 A | 12/1992 | Bregen et al. |
| 5,176,682 A | 1/1993 | Chow |
| 5,193,525 A | 3/1993 | Silverstein et al. |
| 5,199,566 A | 4/1993 | Ortiz et al. |
| 5,203,863 A | 4/1993 | Bidoia |
| 5,207,679 A | 5/1993 | Li |
| 5,207,690 A | 5/1993 | Rohrbacher et al. |
| 5,207,694 A | 5/1993 | Broome |
| 5,211,650 A | 5/1993 | Node |
| 5,213,093 A | 5/1993 | Swindle |
| 5,217,486 A | 6/1993 | Rice et al. |
| 5,220,928 A | 6/1993 | Oddsen |
| 5,224,946 A | 7/1993 | Hayhurst et al. |
| 5,236,445 A | 8/1993 | Hayhurst et al. |
| 5,242,431 A | 9/1993 | Kristiansen |
| 5,254,126 A | 10/1993 | Filipi et al. |
| 5,258,015 A | 11/1993 | Li et al. |
| 5,258,016 A | 11/1993 | DiPoto et al. |
| 5,259,366 A | 11/1993 | Reydel et al. |
| 5,268,001 A | 12/1993 | Nicholson et al. |
| 5,269,789 A | 12/1993 | Chin et al. |
| 5,269,809 A | 12/1993 | Hayhurst et al. |
| 5,273,053 A | 12/1993 | Pohndorf |
| 5,281,236 A | 1/1994 | Bagnato et al. |
| 5,281,237 A | 1/1994 | Gimpelson |
| 5,282,832 A | 2/1994 | Toso et al. |
| 5,284,485 A | 2/1994 | Kammerer et al. |
| 5,290,296 A | 3/1994 | Phillips |
| 5,290,297 A | 3/1994 | Phillips |
| 5,297,536 A | 3/1994 | Wilk |
| 5,304,184 A | 4/1994 | Hathaway et al. |
| 5,306,280 A | 4/1994 | Bregen et al. |
| 5,306,281 A | 4/1994 | Beurrier |
| 5,306,309 A | 4/1994 | Wagner et al. |
| 5,312,438 A | 5/1994 | Johnson |
| 5,320,630 A | 6/1994 | Ahmed |
| 5,324,308 A | 6/1994 | Pierce |
| 5,330,442 A | 7/1994 | Green et al. |
| 5,330,486 A | 7/1994 | Wilk |
| 5,333,624 A | 8/1994 | Tovey |
| 5,334,200 A | 8/1994 | Johnson |
| 5,336,229 A | 8/1994 | Nods |
| 5,344,060 A | 9/1994 | Gravener et al. |
| 5,354,298 A | 10/1994 | Lee et al. |
| 5,356,413 A | 10/1994 | Martins et al. |
| 5,356,416 A | 10/1994 | Chu et al. |
| 5,364,407 A | 11/1994 | Poll |
| 5,364,408 A | 11/1994 | Gordon |
| 5,368,599 A | 11/1994 | Hirsch et al. |
| 5,368,601 A | 11/1994 | Sauer et al. |
| 5,370,662 A | 12/1994 | Stone et al. |
| 5,372,599 A | 12/1994 | Martins |
| 5,372,604 A | 12/1994 | Trott |
| 5,376,101 A | 12/1994 | Green et al. |
| 5,380,334 A | 1/1995 | Torrie et al. |
| 5,383,905 A | 1/1995 | Golds et al. |
| 5,389,103 A | 2/1995 | Melzer et al. |
| 5,391,173 A | 2/1995 | Wilk |
| 5,391,176 A | 2/1995 | Torre |
| 5,391,182 A | 2/1995 | Chin |
| 5,395,030 A | 3/1995 | Kuramoto et al. |
| 5,398,844 A | 3/1995 | Zaslavsky et al. |
| 5,403,346 A | 4/1995 | Loeser |
| 5,403,348 A | 4/1995 | Bonutti |
| 5,405,354 A | 4/1995 | Sarrett |
| 5,405,359 A | 4/1995 | Pierce |
| 5,409,499 A | 4/1995 | Yi |
| 5,411,506 A | 5/1995 | Golbe et al. |
| 5,411,522 A | 5/1995 | Trott |
| 5,411,523 A | 5/1995 | Goble |
| 5,413,585 A | 5/1995 | Pagedasa |
| 5,417,691 A | 5/1995 | Hayhurst |
| 5,417,697 A | 5/1995 | Wilk et al. |
| 5,417,699 A | 5/1995 | Klein et al. |
| 5,423,834 A | 6/1995 | Ahmed |
| 5,423,860 A | 6/1995 | Lizardi et al. |
| 5,431,639 A | 7/1995 | Shaw |
| 5,431,666 A | 7/1995 | Sauer et al. |
| 5,433,722 A | 7/1995 | Sharpe et al. |
| 5,437,680 A | 8/1995 | Yoon |
| 5,437,681 A | 8/1995 | Meade et al. |

| | | | | | | |
|---|---|---|---|---|---|---|
| 5,439,467 A | 8/1995 | Benderev et al. | | 5,827,298 A | 10/1998 | Hart et al. |
| 5,443,482 A | 8/1995 | Stone et al. | | 5,827,306 A | 10/1998 | Yoon |
| 5,445,167 A | 8/1995 | Yoon et al. | | 5,853,416 A | 12/1998 | Tolkoff |
| 5,447,512 A | 9/1995 | Wilson et al. | | 5,860,946 A | 1/1999 | Hofstatter |
| 5,458,608 A | 10/1995 | Wortrich | | 5,860,992 A | 1/1999 | Daniel et al. |
| 5,462,558 A | 10/1995 | Kolesa et al. | | 5,897,487 A | 4/1999 | Ouchi |
| 5,462,559 A | 10/1995 | Ahmed | | 5,899,921 A | 5/1999 | Caspari et al. |
| 5,462,561 A | 10/1995 | Voda | | 5,902,321 A | 5/1999 | Caspari et al. |
| 5,464,426 A | 11/1995 | Bonutti | | 5,910,105 A | 6/1999 | Swain et al. |
| 5,466,241 A | 11/1995 | Leroy et al. | | 5,919,208 A | 7/1999 | Valenti |
| 5,470,337 A | 11/1995 | Moss | | RE36,289 E | 8/1999 | Le et al. |
| 5,474,572 A | 12/1995 | Hayhurst | | 5,931,844 A | 8/1999 | Thompson et al. |
| 5,474,573 A | 12/1995 | Hatcher | | 5,935,149 A | 8/1999 | Ek |
| 5,478,353 A | 12/1995 | Yoon | | 5,938,586 A | 8/1999 | Wilk et al. |
| 5,487,746 A | 1/1996 | Yu et al. | | 5,947,983 A | 9/1999 | Solar et al. |
| 5,507,754 A | 4/1996 | Green et al. | | 5,972,001 A | 10/1999 | Yoon |
| 5,507,758 A | 4/1996 | Thomason et al. | | 5,984,917 A | 11/1999 | Fleischman et al. |
| 5,507,797 A | 4/1996 | Suzuki et al. | | 5,997,556 A | 12/1999 | Tanner |
| 5,514,159 A | 5/1996 | Matula et al. | | 6,001,110 A | 12/1999 | Adams |
| 5,520,700 A | 5/1996 | Beyar et al. | | 6,007,551 A | 12/1999 | Peifer et al. |
| 5,520,702 A | 5/1996 | Saur et al. | | 6,010,515 A | 1/2000 | Swain et al. |
| 5,520,703 A | 5/1996 | Essig et al. | | 6,010,525 A | 1/2000 | Bonutti et al. |
| 5,527,318 A | 6/1996 | McGarry | | 6,015,428 A | 1/2000 | Padedas |
| 5,531,763 A | 7/1996 | Mastri et al. | | 6,024,755 A | 2/2000 | Addis |
| 5,540,705 A | 7/1996 | Meade et al. | | 6,036,694 A | 3/2000 | Goble et al. |
| 5,542,432 A | 8/1996 | Slater | | 6,059,719 A | 5/2000 | Yamamoto et al. |
| 5,545,170 A | 8/1996 | Hart | | 6,059,798 A | 5/2000 | Tolkoff |
| 5,545,180 A | 8/1996 | Le et al. | | 6,066,160 A | 5/2000 | Colvin et al. |
| 5,549,617 A | 8/1996 | Green et al. | | 6,071,233 A | 6/2000 | Ishikawa et al. |
| 5,562,686 A | 10/1996 | Sauer et al. | | 6,071,292 A | 6/2000 | Makower et al. |
| 5,562,689 A | 10/1996 | Green et al. | | 6,074,401 A | 6/2000 | Gardiner et al. |
| 5,569,274 A | 10/1996 | Rapacki et al. | | 6,086,600 A | 7/2000 | Kortenbach |
| 5,569,305 A | 10/1996 | Bonutti | | 6,086,608 A | 7/2000 | Ek et al. |
| 5,571,119 A | 11/1996 | Atala | | 6,099,535 A | 8/2000 | Lamport et al. |
| 5,584,861 A | 12/1996 | Swain et al. | | 6,126,677 A | 10/2000 | Ganaja et al. |
| 5,584,862 A | 12/1996 | Bonutti | | 6,129,661 A | 10/2000 | Iafrati et al. |
| 5,591,177 A | 1/1997 | Lehrer | | 6,136,009 A | 10/2000 | Mears |
| 5,591,180 A | 1/1997 | Hinchliffe | | 6,149,658 A | 11/2000 | Gardiner et al. |
| 5,601,530 A | 2/1997 | Nielsen et al. | | 6,159,234 A | 12/2000 | Bonutti et al. |
| 5,601,571 A | 2/1997 | Moss | | 6,200,329 B1 | 3/2001 | Fung et al. |
| 5,609,597 A | 3/1997 | Lehrer | | 6,238,336 B1 | 5/2001 | Ouchi |
| 5,618,314 A | 4/1997 | Harwin et al. | | 6,241,140 B1 | 6/2001 | Adams et al. |
| 5,624,453 A | 4/1997 | Ahmed | | 6,280,452 B1 | 8/2001 | Mears |
| 5,626,590 A | 5/1997 | Wilk | | 6,346,111 B1 | 2/2002 | Gordon et al. |
| 5,630,824 A | 5/1997 | Hart | | 6,352,503 B1 | 3/2002 | Matsui et al. |
| 5,645,553 A | 7/1997 | Kolesa et al. | | 6,358,259 B1 | 3/2002 | Swain et al. |
| 5,658,313 A | 8/1997 | Thal et al. | | 6,406,424 B1 | 6/2002 | Williamson et al. |
| 5,665,096 A | 9/1997 | Yoon | | 6,436,108 B1 | 8/2002 | Mears |
| 5,665,109 A | 9/1997 | Yoon | | 6,443,962 B1 | 9/2002 | Gaber |
| 5,665,112 A | 9/1997 | Thal | | 6,454,778 B2 | 9/2002 | Kortenbach |
| 5,681,328 A | 10/1997 | Lamport et al. | | 6,494,888 B1 | 12/2002 | Laufer et al. |
| 5,681,351 A | 10/1997 | Jamiolkowski et al. | | 6,506,196 B1 | 1/2003 | Laufer |
| 5,683,417 A | 11/1997 | Cooper | | 6,514,265 B2 | 2/2003 | Ho et al. |
| 5,683,419 A | 11/1997 | Thal | | 6,551,332 B1 | 4/2003 | Nguyen et al. |
| 5,683,464 A | 11/1997 | Wagner et al. | | 6,558,400 B2 | 5/2003 | Deem et al. |
| 5,693,060 A | 12/1997 | Martin | | 6,607,541 B1 | 8/2003 | Gardiner et al. |
| 5,695,505 A | 12/1997 | Yoon | | 6,626,930 B1 | 9/2003 | Allen et al. |
| 5,697,940 A | 12/1997 | Chu et al. | | 6,629,630 B2 | 10/2003 | Adams |
| 5,702,397 A | 12/1997 | Goble et al. | | 6,656,194 B1 | 12/2003 | Gannoe et al. |
| 5,709,693 A | 1/1998 | Taylor | | 6,663,639 B1 | 12/2003 | Laufer et al. |
| 5,713,910 A | 2/1998 | Gordon et al. | | 6,689,130 B2 | 2/2004 | Arai et al. |
| 5,720,765 A | 2/1998 | Thal | | 6,719,763 B2 | 4/2004 | Chung et al. |
| 5,728,136 A | 3/1998 | Thal | | 6,719,764 B1 | 4/2004 | Gellman et al. |
| 5,730,747 A | 3/1998 | Ek et al. | | 6,736,828 B1 | 5/2004 | Adams et al. |
| 5,735,793 A | 4/1998 | Takahashi et al. | | 6,746,460 B2 | 6/2004 | Gannoe et al. |
| 5,735,877 A | 4/1998 | Pagedes | | 6,755,843 B2 | 6/2004 | Chung et al. |
| 5,741,281 A | 4/1998 | Martin | | 6,773,440 B2 | 8/2004 | Gannoe et al. |
| 5,741,301 A | 4/1998 | Pagedas | | 6,835,200 B2 | 12/2004 | Laufer et al. |
| 5,752,963 A | 5/1998 | Allard et al. | | 6,908,427 B2 | 6/2005 | Fleener et al. |
| 5,755,730 A | 5/1998 | Swain et al. | | 6,923,819 B2 | 8/2005 | Meade et al. |
| 5,766,186 A | 6/1998 | Faraz et al. | | 7,615,060 B2 | 11/2009 | Stokes et al. |
| 5,782,776 A | 7/1998 | Hani | | 7,628,796 B2 | 12/2009 | Shelton, IV et al. |
| 5,782,823 A | 7/1998 | Mueller | | 2002/0107530 A1 | 8/2002 | Sauer et al. |
| 5,788,715 A | 8/1998 | Watson, Jr. et al. | | 2002/0116010 A1 | 8/2002 | Chung et al. |
| 5,792,153 A | 8/1998 | Swain et al. | | 2002/0177847 A1 | 11/2002 | Long et al. |
| 5,810,853 A | 9/1998 | Yoon | | 2003/0083674 A1 | 5/2003 | Gibbens, III |
| 5,810,854 A | 9/1998 | Beach | | 2003/0167062 A1 | 9/2003 | Gambale et al. |
| 5,814,056 A | 9/1998 | Prosst et al. | | 2003/0171651 A1 | 9/2003 | Page et al. |
| 5,814,071 A | 9/1998 | McDevitt et al. | | 2003/0171760 A1 | 9/2003 | Gambale et al. |

| Pub. No. | Date | Inventor |
|---|---|---|
| 2003/0176880 A1 | 9/2003 | Long et al. |
| 2003/0181924 A1 | 9/2003 | Yamamoto et al. |
| 2003/0208209 A1 | 11/2003 | Gambale et al. |
| 2003/0233104 A1 | 12/2003 | Gellman et al. |
| 2003/0233108 A1 | 12/2003 | Gellman et al. |
| 2004/0034369 A1 | 2/2004 | Sauer et al. |
| 2004/0034371 A1 | 2/2004 | Lehman et al. |
| 2004/0044354 A1 | 3/2004 | Gannoe et al. |
| 2004/0059350 A1 | 3/2004 | Gordon et al. |
| 2004/0082963 A1 | 4/2004 | Gannoe et al. |
| 2004/0088008 A1 | 5/2004 | Gannoe et al. |
| 2004/0092960 A1 | 5/2004 | Abrams et al. |
| 2004/0122473 A1 | 6/2004 | Ewers et al. |
| 2004/0138682 A1 | 7/2004 | Onuki et al. |
| 2004/0138704 A1 | 7/2004 | Gambale et al. |
| 2004/0147941 A1 | 7/2004 | Takemoto et al. |
| 2004/0147958 A1 | 7/2004 | Lam et al. |
| 2004/0158125 A1 | 8/2004 | Aznoian et al. |
| 2004/0162568 A1 | 8/2004 | Saadat et al. |
| 2004/0194790 A1 | 10/2004 | Laufer et al. |
| 2004/0210243 A1 | 10/2004 | Gannoe et al. |
| 2004/0260344 A1 | 12/2004 | Lyons et al. |
| 2005/0015101 A1 | 1/2005 | Gibbens, III et al. |
| 2005/0033319 A1 | 2/2005 | Gambale et al. |
| 2005/0055038 A1 | 3/2005 | Kelleher et al. |
| 2005/0070931 A1 | 3/2005 | Li et al. |
| 2005/0075653 A1 | 4/2005 | Saadat et al. |
| 2006/0020167 A1 | 1/2006 | Sitzmann |
| 2006/0069396 A1 | 3/2006 | Meade et al. |
| 2006/0282095 A1 | 12/2006 | Stokes et al. |
| 2011/0152890 A1 | 6/2011 | Newell et al. |

FOREIGN PATENT DOCUMENTS

| | | |
|---|---|---|
| DE | 3909999 A1 | 9/1990 |
| DE | 4310315 A1 | 10/1993 |
| EP | 0591991 A2 | 4/1994 |
| EP | 0598219 A2 | 5/1994 |
| EP | 1582138 | 10/2005 |
| EP | 1584295 | 10/2005 |
| EP | 1586275 | 10/2005 |
| EP | 1639936 | 3/2006 |
| EP | 1839591 | 10/2007 |
| EP | 1839593 | 10/2007 |
| GB | 2165559 | 4/1986 |
| GB | 2200072 A | 7/1988 |
| JP | S55-166142 A1 | 12/1980 |
| JP | 61-122852 | 6/1986 |
| JP | 6-047050 | 2/1994 |
| JP | 7-136177 | 5/1995 |
| JP | H09-507421 A1 | 7/1997 |
| JP | 10-500318 | 1/1998 |
| JP | H10-506559 A1 | 6/1998 |
| WO | WO 95/25468 | 9/1995 |
| WO | WO 96/09796 | 4/1996 |
| WO | WO 96/20647 | 7/1996 |
| WO | WO 97/29694 | 8/1997 |
| WO | WO 99/12482 | 3/1999 |
| WO | WO 99/22650 | 5/1999 |
| WO | WO 99/47050 | 9/1999 |
| WO | WO 00/61012 | 10/2000 |
| WO | WO 01/10312 | 2/2001 |
| WO | WO 01/66001 | 9/2001 |
| WO | WO 01/66018 A | 9/2001 |
| WO | WO 01/87144 | 11/2001 |
| WO | WO 01/89370 | 11/2001 |
| WO | WO 01/89393 A | 11/2001 |
| WO | WO 02/35980 | 5/2002 |
| WO | WO 03/090630 | 11/2003 |
| WO | WO 2004/014237 | 2/2004 |
| WO | WO 2004/021894 | 3/2004 |
| WO | WO 2004/037064 | 5/2004 |

OTHER PUBLICATIONS

Cook® Wilson-Cook Medical GI Endoscopy, Sales Literature, www.wilsoncook.com.

Filipi, "Transoral flexible endoscopic suturing for treatment of GERD: A multicenter Trial", *Gastrointest. Encosc.* (Apr. 2001), vol. 53, No. 4, 416-422.

Lehman et al. "Endoscopic gastroesophageal suturing: Does addition of cautery aid plication persistence?" *Digestive Disease Week* Poster Board Presentation (May 2000), on-line Abstract (Feb. 2000).

Martinez-Serna et al., "Endoscopic valvuloplasty for GERD," *Gastrointest. Endosc.*, (Nov. 2000) vol. 52, No. 5, 663-70.

Sherman et al., "Efficacy of endoscopic sphincterotomy and surgical sphincteroplasty for patients with sphincter of Oddi dysfunction: randomized prospective study," *Gastrointest. Endosc.*, vol. 37, No. 2 (1991) 249 (Abstract).

Sherman et al., "Endoscopic sphincterotomy induced hemorrhage: treatment with multipolar electrocoagulation", *Gastrointest. Endosc.*, vol. 37, No. 2 (1991) 249 (Abstract).

European Examination Report for European Application No. 03754465.7, dated Jul. 16, 2008.

English translation of Notice of Reasons for Rejection, mailed on Sep. 8, 2009, for Japanese Patent Application No. 2004-534766 (4 pages).

European search report, mailed Mar. 12, 2008, for European Patent Application No. EP 03 75 4465.

English translation of Notice of Reasons for Rejection, mailed on Sep. 10, 2010, for Japanese Patent Application No. 2004-534766 (2 pages).

Office Action Summary (PTOL-326)(1 page), p. 2 of Amendments to the Claims (1 page) and Screenshot from Continuity Data page of USPTO website (1 page) from U.S. Appl. No. 11/394,127, Submitted to the office on Jul. 23, 2010.

* cited by examiner

INTEGRATED ENDOSCOPE AND ACCESSORY TREATMENT DEVICE

RELATED APPLICATIONS

This application is a divisional of U.S. patent application Ser. No. 12/072,441, filed Feb. 26, 2008, which is a continuation of U.S. patent application Ser. No. 10/658,135, filed Sep. 8, 2003, which claims the benefit of U.S. Provisional Application No. 60/408,556, filed on Sep. 6, 2002, the subject matter of which is related to the disclosure document filed at the U.S. Patent and Trademark Office on Sep. 7, 2000, and assigned Disclosure Document No. 479631.

FIELD OF THE INVENTION

This invention relates to endoscopes and devices and methods for carrying out medical treatments using an endoscope.

BACKGROUND OF INVENTION

Viewing endoscopes permit remote treatment of internal locations within a patient by accessing those locations through a natural body lumen avoiding the need for surgery in some cases. The advantages of using an endoscope to treat internal maladies of the human body has led to the development of various endoscopic accessory treatment devices that can be fastened to the distal end of the endoscope to carry out mechanical manipulation and treatment of internal tissue areas. Examples of such endoscopic accessories include suturing devices, cutting instruments, band ligating devices and forceps, among others. The accessories are securable to various types of endoscopes specifically designed for specific areas of the body and include: laparoscopes, duodenoscopes, colonoscopes, sigmoidoscopes, bronchoscopes, and urethroscopes, among others. In combination with remote viewing capability, endoscopes are frequently configured to provide a working channel through which controls for the scope mounted accessory may be inserted for remote operation.

Although an endoscope carrying a treatment accessory provides remote treatment capability while permitting direct visualization of the treatment site, several shortcomings may arise in the use of the combination. First, the separate accessory may limit viewing capability through the distal end of the endoscope when it is attached so as to extend distally from the distal face of the endoscope. Second, there is always a risk that the accessory will become detached from the endoscope while in the patient, compromising the procedure and presenting problems for safely removing the detached accessory from the patient. Third, with various manufacturers producing endoscopes and accessories of differing diameters, mounting a particular accessory to an endoscope can be problematic if their diameters are not compatible. Fourth, the control mechanisms for operating the accessory must extend through existing working channels in the endoscope interfering with or prohibiting introduction of additional accessories or instruments through the endoscope during the procedure. Also, the accessory controls may be awkward to mount and operate in conjunction with the endoscope as the endoscope was not originally designed to accommodate such additional controls.

It would be advantageous to provide an endoscope and operative treatment accessory that are designed to operate together to avoid the problems mentioned above encountered with separate devices. It is an object of the present invention to provide an integrated endoscope and treatment accessory in a single structure that overcomes the shortcomings of the prior art devices mentioned above.

SUMMARY OF INVENTION

The present invention provides an integrated endoscope and treatment accessory that is secure, reliable and easy to operate accurately. The device comprises an endoscope shaft configured similarly to conventional endoscope shafts and may be provided with a working channel, a channel for optical fibers for viewing capability and light transmission as well as auxiliary channels to provide viewing lens cleaning or additional working channel capability. The endoscope shaft further provides along its length space for the operative control elements of the integrated treatment device placed at the distal end of the endoscope. The treatment device may consist of a housing in which separate, movable components are arranged to carry out the specified medical treatment or procedure. Elements extending through the shaft of the endoscope such as cables, wires, or fluid pressure serve to operate the components of the accessory. Because the accessory is integrated into the endoscope, the viewing elements can be specifically arranged to provide viewing capability of the location of the accessory where treatment will be carried out on tissue. Additionally, with control elements for the accessory being integrated into the endoscope shaft, separate open working channels can be left free to receive other devices or instruments in the overall diameter of the endoscope shaft need not be increased dramatically by an externally applied accessory control sheath or catheter.

The integrated endoscope and accessory may employ any type of treatment device presently known to be applicable to an endoscope as a separately attached accessory. Specifically, the integrated accessory may comprise forceps, a mechanical or electrical cutting element, suturing device, band ligating device or other tissue manipulating mechanism. The housing for the accessory is integrated into the shaft of the endoscope near its distal end appropriately positioned along the shaft for the treatment that will be carried out. The control mechanisms for operating the accessory may be similar to conventional specific accessories but will extend through spaces that are specifically formed through the endoscope to accommodate them. At the proximal end of the endoscope, an integrated control mechanism can be employed adjacent the endoscope distal end control mechanisms so that a user can operate both sets of controls easily. Alternatively, the accessory controls can be integrated with the endoscope controls for ease of use. Further the accessory controls can be positioned at any convenient location along the length of the endoscope where the physician would ordinarily grasp the endoscope shaft to control its movement in the patient.

Although the integrated accessory may comprise any type of treatment device known to be usable with endoscopes, the following detailed description illustrates the example of an integrated endoscope and accessory device through the example of a tissue suturing device integrated into a gastroscope. It will be understood that those skilled in the art that the examples provided herein can be easily modified to accommodate other types of accessories for practicing other types of treatments.

It is an object of the invention to provide an integrated endoscope and medical treatment device accessory.

It is another object of the invention to provide a method for using an integrated endoscope and medical treatment device accessory that reduces the number of steps and instruments required to complete an endoscopic procedure

BRIEF DESCRIPTION OF THE DRAWINGS

The foregoing and other objects and advantages of the invention will be appreciated more fully from the following further description thereof, with reference to the accompanying diagrammatic drawings wherein.

DESCRIPTION OF THE ILLUSTRATIVE EMBODIMENTS

The present invention provides an endoscope with an integrated medical device treatment accessory at its distal end. The devices contemplated for integration with the endoscope include tissue apposition devices, forceps or tissue cutting instruments. Several embodiments of the integrated endoscope employing tissue apposition devices are presented below.

In one embodiment of the integrated endoscope, the tissue apposition device as disclosed in U.S. Pat. No. 5,792,153 may be employed. The '153 patent is incorporated by reference herein in its entirety. A brief explanation of the configuration and operation of the prior art tissue apposition device is presented with reference to the prior art FIGS. 1-3.

Figure 1:
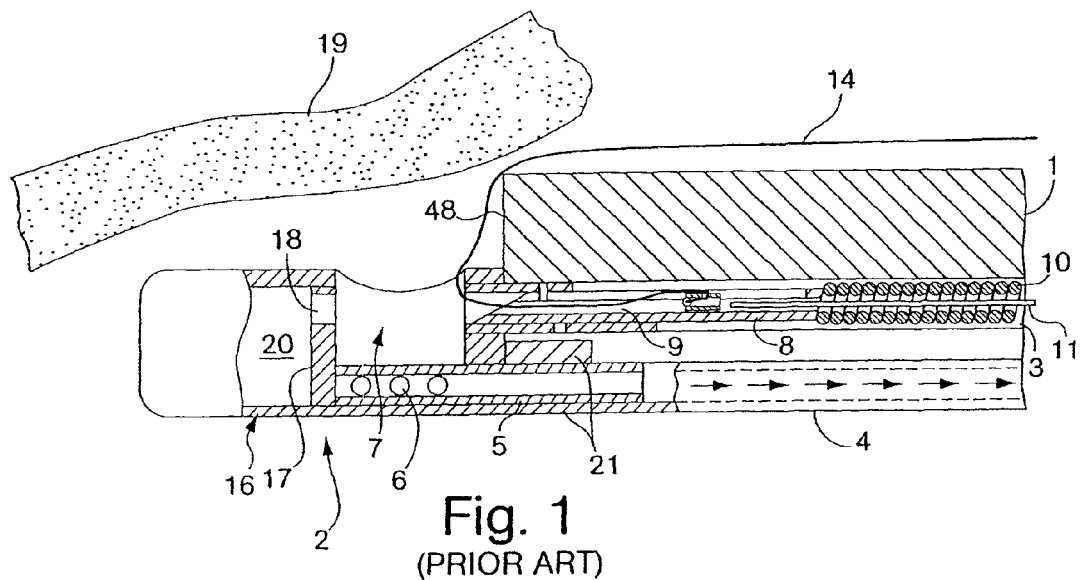
FIGS. 1-3 show successive steps in the operation of a prior art single stitch sewing device.
Figure 2:
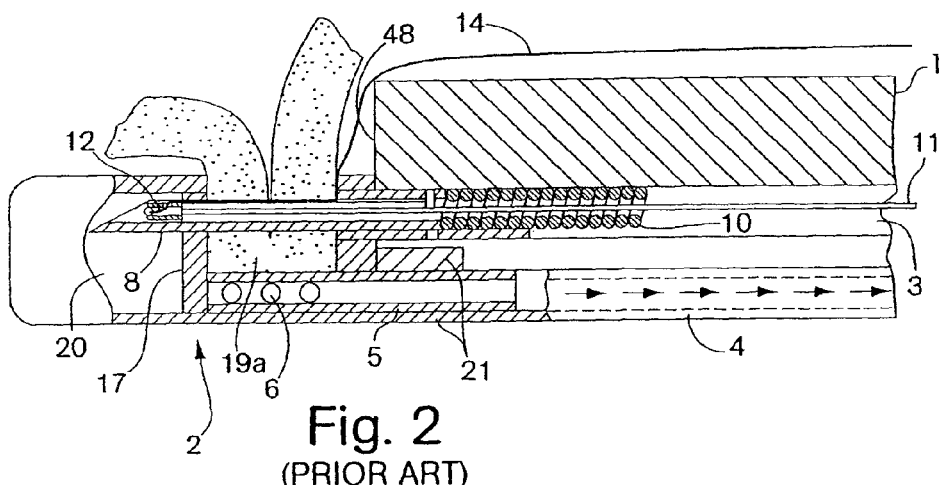
Figure 3:
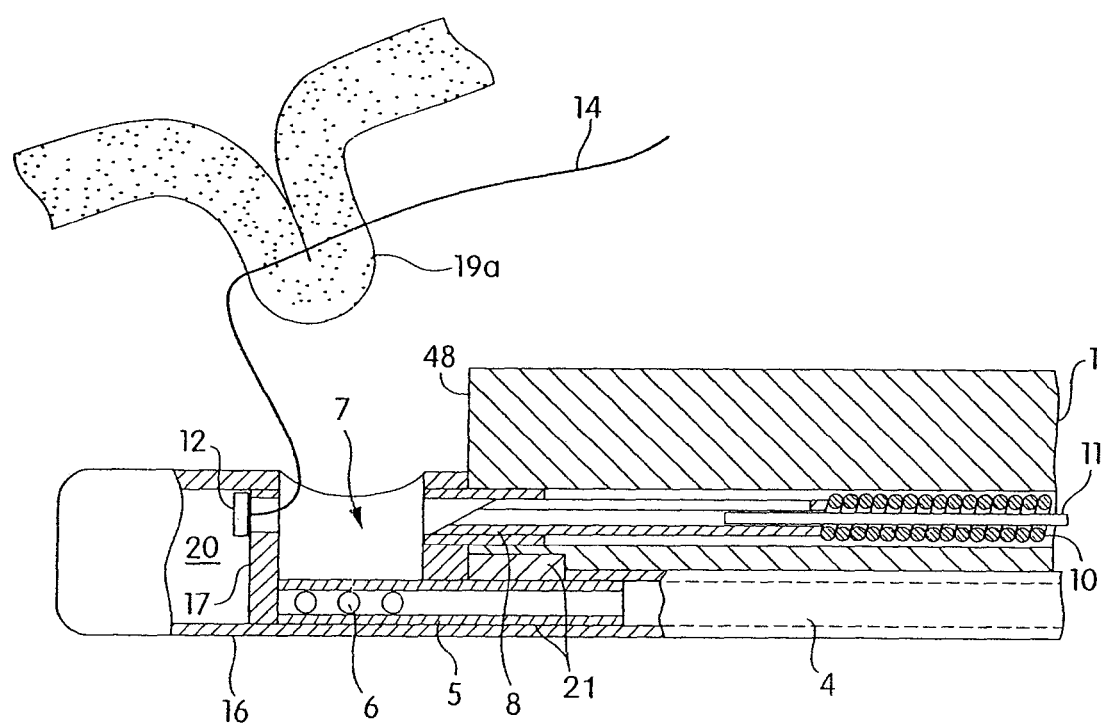

FIGS. 1-3 depict a prior art endoscopic suturing device disclosed in U.S. Pat. No. 5,792,153. FIG. 1 shows the distal end of a flexible endoscope 1, on which a sewing device 2 is attached. The endoscope is provided with a viewing channel, which is not shown, but which terminates at a lens on the distal face of the endoscope. The endoscope is further provided with a biopsy or working channel 3, and a suction channel 4 the proximal end of which is connected to a source of vacuum (not shown). The suction channel 4 may comprise a separate tube that runs along the exterior of the endoscope, rather than an internal lumen as shown. The sewing device 2 has a tube 5, which communicates with the suction pipe 4 and has a plurality of perforations 6 therein. These perforations communicate with an upwardly open vacuum chamber 7 formed in the sewing device.

Figure 1A:
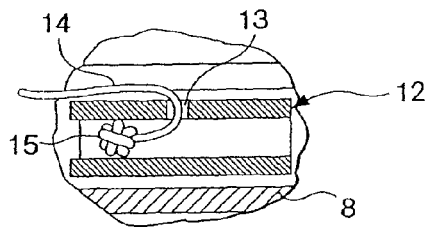

A hollow needle 8 is mounted in the biopsy channel 3, with its beveled tip extending into the sewing device. The needle has a channel 9 extending therethrough. A flexible, wire-wound cable 10 has its forward end attached to the rear of the needle 8, and a center wire 11 runs within the cable 10, along the entire length thereof, and is longitudinally movable with respect thereto. The diameter of the wire 11 is such that it is longitudinally movable within the channel 9 and, in the position shown in FIG. 1, the forward end portion of the wire 11 extends into the rear end portion of the channel 9. A thread carrier in the form of a tag 12 is slidably and releasably mounted in the channel 9. The tag is shown in detail in FIG. 1A. The tag is hollow and has an aperture 13 extending through the sidewall thereof. As can also be seen in FIG. 1, one end of a thread 14 is secured to the tag by passing it through the aperture 13 and tying in the end of a knot 15 of sufficient size to prevent the thread escaping from the tag. The tag may be made from a relatively rigid material such as stainless steel.

At the distal end of the sewing device is defined a hollow head portion 16 defining a chamber 20 therein. Between the chamber 20 and the cavity 7 is a wall 17, in which an aperture 18 is formed. The aperture 18 has a diameter that is marginally greater than the external diameter of the needle 8, and is aligned therewith. The clearance between the needle 8 and the aperture 18 must be sufficiently small to prevent tissue being forced through the aperture and causing the needle to jam. Finally, FIG. 1 shows a portion of the patient's tissue 19, in which a stitch is to be formed.

In operation, suction is applied to the suction pipe 4, and thence, via the perforations 6 in the tube 5 to the cavity 7. This sucks into the cavity a U-shaped portion 19a of the tissue 19, as shown in FIG. 2. The hollow needle 8 is pushed through the U-shaped tissue portion 19a by extending distally the wire-wound cable 10 and associated needle 8. After full advancement of the needle through both folds of the U-shaped tissue portion, the tip portion of the needle 8 is distal to the wall 17 and within the chamber 20 in the hollow head portion 16. Distal movement of wire 11, slidably received within the wound cable 10, pushes the tag 12 out of the channel 9 and into the chamber 20 where it rotates out of alignment with aperture 18 to become captured in the chamber.

The wire 11 is then withdrawn proximally, followed by proximal withdrawal of the cable 10, to withdraw the needle 8 from the tissue portion 19a. The suction is then discontinued allowing the U-shaped tissue portion 19a to be released from the cavity 7. As shown in FIG. 3, the released tissue is left with a suture thread 14 passing through the two layers of tissue that form the U-shaped fold 19a. One end of the suture is joined to the tag 12 that remains captured in the chamber 20 and the other end of the suture extends through the patient's esophagus and out of the mouth. Finally, the endoscope and sewing device are withdrawn from the patient. In so doing, the thread 14 is pulled partially through the tissue portion 19a, as the captured tag 12 is withdrawn proximally and brought outside the patient. With both ends of the thread 14 outside of the patient, the thread can be knotted and the knot endoscopically pushed down to the suture site and severed by an endoscopic knot pusher such as that disclosed in U.S. Pat. No. 6,010,515 (Swain et al).

Figure 4A:
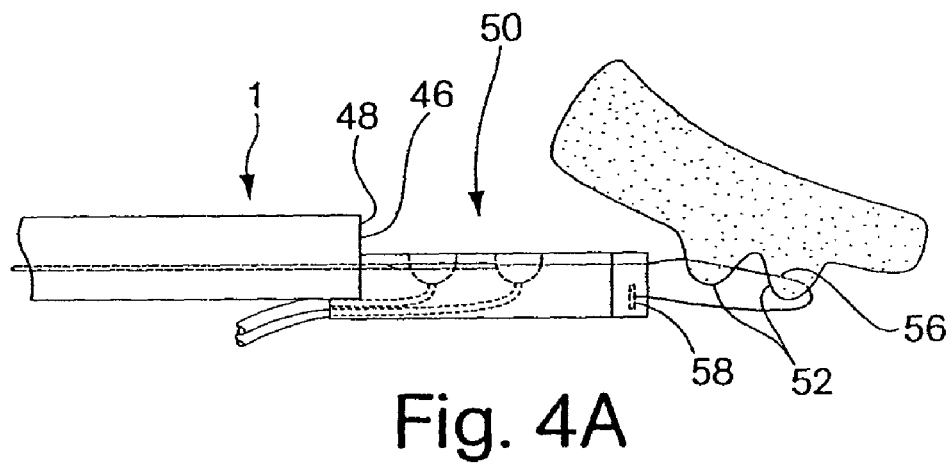
FIGS. 4A-4D are views of multiple suction port apposition devices in various stages of operation.
Figure 4B:
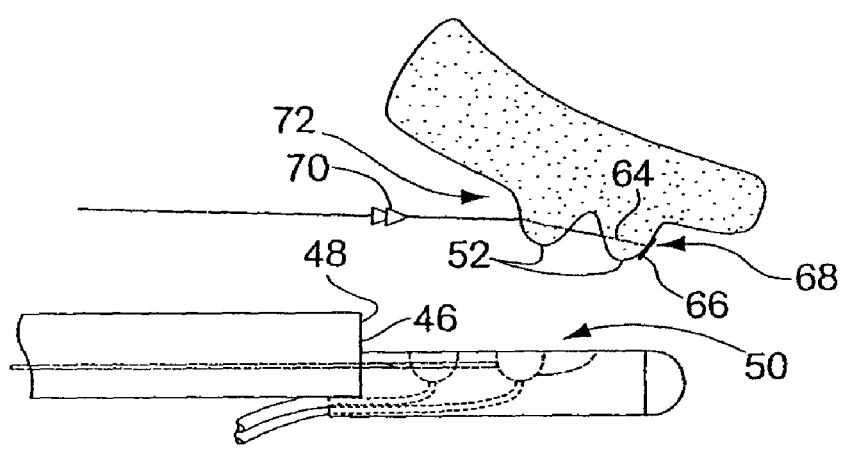
Figure 4C:
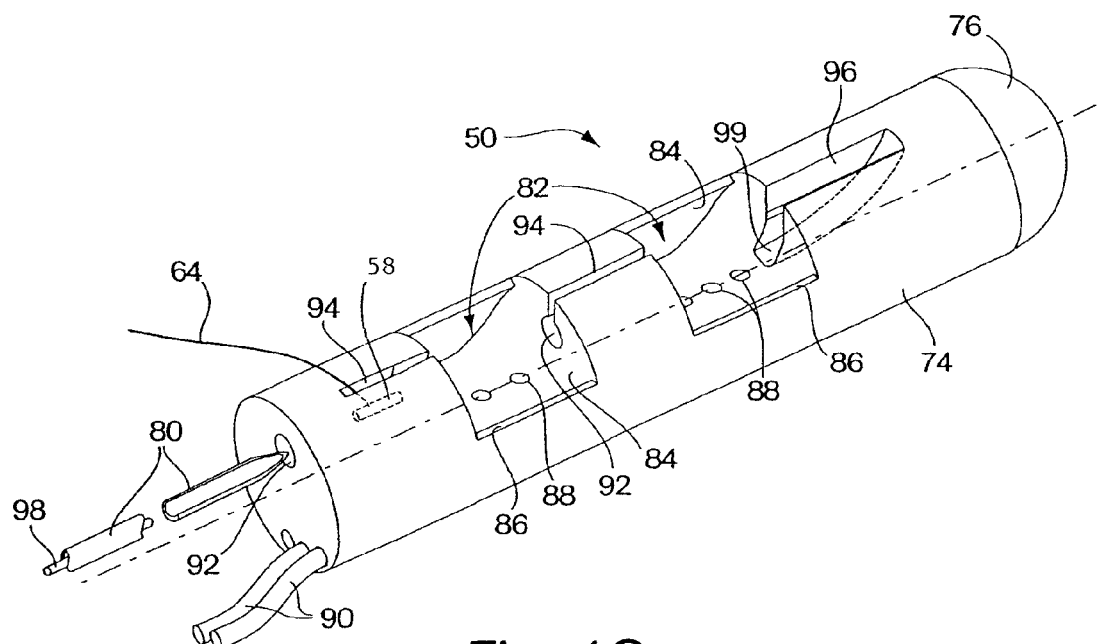

For certain treatments, capturing multiple tissue portions, gathering and holding them together may be desirable. FIGS. 4A-4C illustrate the operation of a multiple suction port apposition device 50 as disclosed in co-pending U.S. application Ser. No. 10/220,379. The '379 patent application is incorporated by reference herein in its entirety. The device can capture multiple tissue portions 52 simultaneously for application of a tissue securing device, such as a suture, tag or staple. The device may be modified to deliver the tissue securing devices of the present invention. Securing two tissue portions 52 in the same number of steps that the prior art device requires to secure a single tissue portion doubles efficiency, reducing the total number of endoscopic intubations required to complete the procedure and reducing the time needed to complete the procedure. Though dual suction port embodiments are discussed for illustration purposes, it should be understood that the multiple port device also could be configured to have three or more suction ports.

The dual suction port tissue apposition device shown in FIG. 4A passes through both tissue portions a suture 56 with a tag 58 capturable in the end cap 60 of the sewing capsule 62, in similar fashion to the prior art device discussed in connection with FIGS. 1-3 above. The dual suction port tissue apposition device shown in FIG. 4B passes through both tissue portions a suture 64 having a permanent tag 66 at its end. In this embodiment, the permanent tag is not captured by the suturing device to later provide a lead for tying a surgical knot. Rather, the permanent tag remains in the body, anchored on the through side 68 of the distal tissue portion. The tissue portions may then secured tightly together, not by a surgical knot, but by a frictionally engageable two piece suture lock device 70 advanced along the single suture lead 64 to abut the proximal side 72 of the tissue portion.

In one embodiment of the multiple suction port device, the multiple suction ports are defined in line on the sewing device, along a common longitudinal axis that is parallel to the longitudinal axis of the device. An isometric view of an in-line dual suction port endoscopic tissue apposition device 50 is shown in FIG. 4C. In FIG. 4C, a slotted and beveled hypodermic suturing needle 80 is in the fully retracted position, with suture tag 58 not yet loaded, and the capsule ready to receive tissue. The sewing device 50 is characterized by a tubular body or capsule 74 that is machined from metal or injection molded from a rigid polymer material. The body may be formed with an atraumatic distal tip 76 to avoid injury to the walls of a body lumen through which the device is delivered.

A plurality of suction ports 86 are formed into the body along its length. Suction ports 86 are large openings defined through the capsule 74, and open to one or more vacuum chambers 82. The chambers are defined in the capsule by surfaces forming sidewalls 84. Communication of the suction ports with the vacuum chambers 82 permits vacuum to reach tissue that is adjacent to the ports to accomplish capture of tissue portions 52 into the chamber. Any number of suction ports can be formed on the capsule body. However, two suction port devices are shown here as illustrative examples because often in the treatment of GERD, a series of two tissue mounds joined together are formed along the stomach wall, below the Z-line. Though more ports and chambers can be formed on the body, the extra body length they would require in the in-line embodiment could potentially present difficulty during navigation of the rigid body through the curves of a natural body lumen.

Tissue portions are drawn into the suction ports and into the vacuum chambers by suction introduced to the chambers through air passages 88. The air passages are open to independent internal channels in the body that are joined to vacuum lines 90. The vacuum lines extend from the proximal end of the capsule body, external to the endoscope, to the proximal end of the scope. Outside the patient, the vacuum lines can be joined to a portable or institutional vacuum source (not shown). A control valve may be inserted in-line near the proximal end of the tubes for selective control of the vacuum by the user. The air passages of all chambers may be joined and controlled by a single vacuum line. Alternatively, as shown in FIG. 4C, separate vacuum lines may be used to supply suction to the air passages of different vacuum chambers. Use of separate vacuum lines permits independent control of suction provided to the several chambers by the use of separate control valves for each vacuum tube at their proximal ends.

Independent vacuum supply to the air passages of each chamber not only helps to ensure adequate vacuum pressure to each chamber, but also permits sequential suctioning of tissue into the chambers. When tissue is collected into both chambers simultaneously, the distal chamber is blocked from the viewing lens 48 on the distal face 46 of the endoscope 1, as shown in FIG. 4B. Therefore, the physician is unable to visually determine whether tissue has been adequately collected into the vacuum chamber so that the needle 80 can be safely advanced through. By applying vacuum first to the distal chamber, tissue collection into that chamber can be visually verified before the view is blocked by tissue entering the proximal chamber. Next, vacuum can be applied to the proximal chamber to capture tissue so that tissue is collected in both chambers simultaneously and held in readiness for penetration by the suture needle (or staple) through both tissue portions with one stroke. However, even with independent vacuum lines, it is possible, and may be desirable to apply a vacuum to all chambers simultaneously.

Figure 4D:
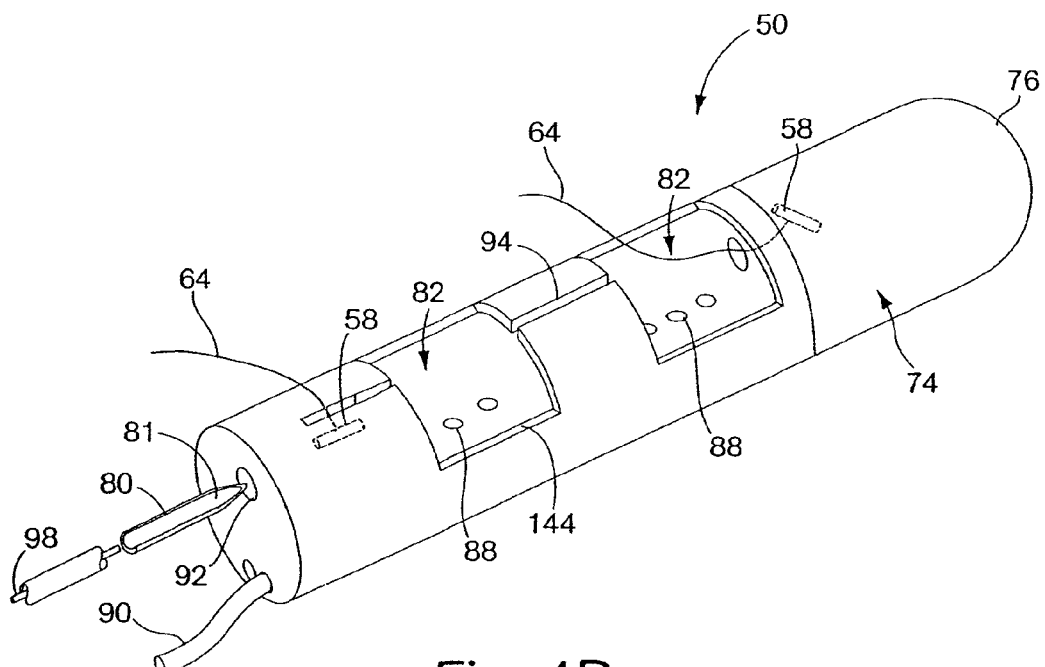

The needle 80 is longitudinally slidable through the capsule body 50, as in the prior art devices. In the in-line dual chamber embodiment shown in FIG. 4C, a tunnel-like needle track 92 extends longitudinally through solid portions in the upper half of the body, not otherwise defined by the vacuum chambers. From the needle track, a thin suture channel 94 extends upwardly through the top surface of the capsule body to provide a space through which the suture lead 64 may pass as the suture tag 58 is advanced by the needle through the needle track 92. The channel 94 is only a sufficient width to permit the suture to pass but is too small to permit passage of the larger needle or suture tag 58. The small dimension of the channel helps maintain the needle and suture tag with in the needle track until they are extended distal to the most distal chamber. An enlarged exit channel 96 extends upwardly from the needle track along the body a short distance distally from the distal chamber 82. The enlarged channel facilitates exit of the suture tag 58 from the body, to follow the released tissue to which it has been attached after being ejected from the extended needle 80 by pusher wire 98. Additionally, a ramp 99 may be formed in the bottom surface of the needle track along the length of the exit channel 96. Extending upwardly as it extends distally, the ramp 99 helps guide an ejected tag up and out from the exit channel and away from the capsule body. A detailed isometric view of the dual suction chamber device of FIG. 4A in which the tag 58 is captured in the distal end 76 of the device is shown in FIG. 4D.

Figure 5A:
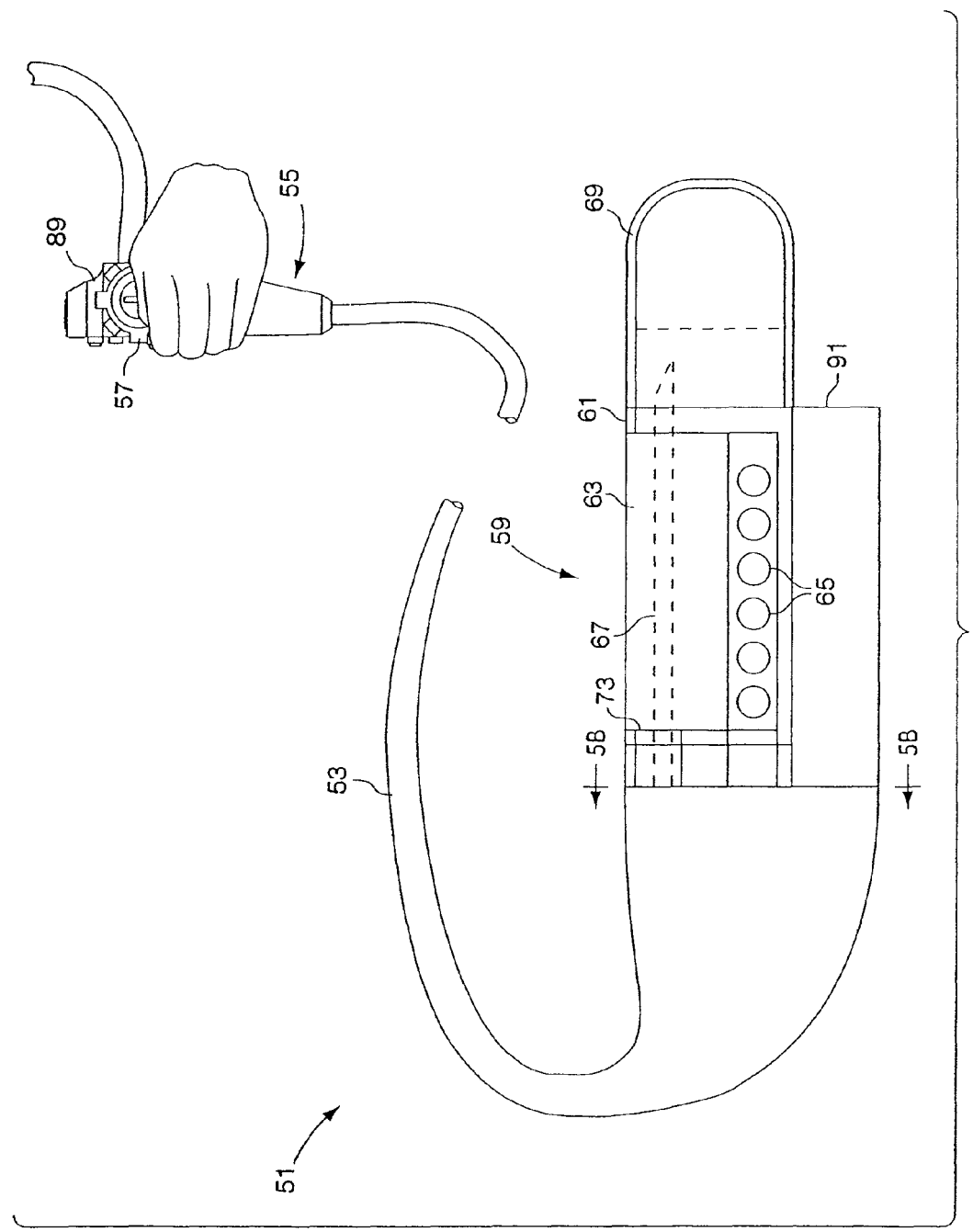
FIG. 5A is a partial sectional side view of an integrated endoscope and treatment device accessory.

The prior art tissue apposition devices may be integrated with the endoscope shaft as shown in FIG. 5A, which presents a sectional view of the distal tip of the endoscope, through the working end of the apposition component. The integrated endoscope 51, shown in FIG. 5A, comprises an endoscope shaft 53 and handle 89 having controls 57 for articulation of the endoscope distal tip 59. Also integrated into handle 89 at the proximal end 55 of the endoscope shaft may be controls for the operation of the accessory, including controls configured as shown in U.S. Pat. No. 5,910,105, incorporated by reference herein in its entirety.

The tissue apposition device 61 located at the distal end 59 of the endoscope is configured similarly to the device discussed in connection with FIGS. 1-3 above. The apposition portion 61 comprises a vacuum chamber 63 into which aspirated tissue is collected in a plurality of suction ports 65 along the bottom of the vacuum chamber 63 for introduction of vacuum to selectively capture tissue into the chamber. The vacuum chamber 63 may be formed from transparent polymer materials to improve visibility of the tissue as captured into the chamber and illumination provided by several light ports integrated into the endoscope. Shown in phantom in FIG. 5A is a needle pathway 67 along which the needle may be moved longitudinally through a captured tissue portion. Beneath the chamber, the endoscope continues distally and terminates at distal face 91. At the distal tip of the apposition portion is provided a removable cap 69, which provides a chamber into which a suture carrying tag may be injected as discussed above in the operation of the prior art device of FIGS. 1-3.

Figure 5B:
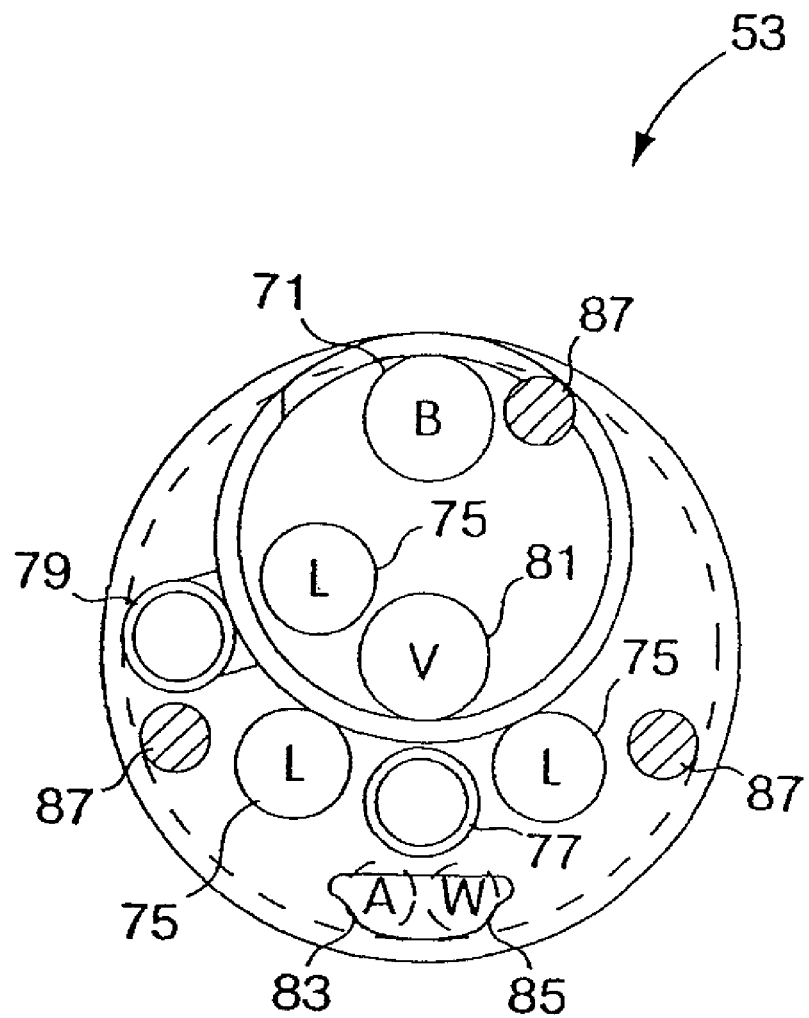
FIG. 5B is a sectional view of the integrated endoscope of FIG. 5A taken along the line 5B-5B.

FIG. 5B is a sectional view of the integrated endoscope shaft 53 taken along the line 5B-5B in FIG. 5A. In the sectional view, an exemplary arrangement of channels and endoscope components is shown. It should be understood that other arrangements of the channels and components may be employed and such alternate arrangements should not be considered to depart from the spirit of the present invention. The several channels and components shown in FIG. 5A each extend the full length of the endoscope shaft 53 from the proximal end 55 where they may be accessed or controlled by the user, through to the distal end 59 of the shaft at the apposition portion 61.

A biopsy channel 71 is provided through which the needle end control wire to move the needle 67 may be inserted. The biopsy channel may measure a diameter of approximately 0.110 inches. Several light channels 75 are provided through which optical fibers pass to transmit light from the proximal end 55 of the endoscope to the working apposition portion of the endoscope. One fiber terminating at the proximal wall 73 of the vacuum chamber 63. Two other light channels terminating at distal face 91. A main objective lens 77 for viewing is provided and carries an optical fiber through the endoscope shaft to the proximal end 55 of the endoscope. Additionally, a side viewing objective lens 79 may be provided, also carrying an optical fiber through the endoscope shaft 53 to the proximal end 55. An internal vacuum line 81 provides vacuum at the distal end 59 of the endoscope shaft from a vacuum connection at the proximal end 55. Additionally, air and water ports 83 and 85 may be provided through the shaft for providing cleaning means for the main viewing lens 77.

Several articulation wires 87 are also provided through the endoscope shaft 53 for the purpose of bending and curving the distal portion of the shaft as it is navigated to the treatment site. The articulation wires are anchored near the distal portion 59 of the endoscope shaft and extend proximally to the control knobs 57 on the handle 89 of the endoscope. It is noted that though the endoscope shaft 53 may be made flexible, the distal working portion 59 comprising the apposition device 61 will be rigid to ensure smooth movement of the rigid needle 67 required for tissue penetration. Accordingly, the articulation of the endoscope shaft will be just proximal to the apposition portion. With the exemplary lumens and components described above, it is expected that the endoscope shaft will have an outside diameter on the order of 0.550 inches. Finally, it is noted that the above-described embodiment can be carried out in an apposition portion 61 having multiple vacuum chambers 63 as is shown in FIGS. 4A-D. Details of the operation and configuration of the multiple chamber apposition device may be found in U.S. patent application Ser. No. 10/220,379, incorporated by reference herein in its entirety.

Figure 6:
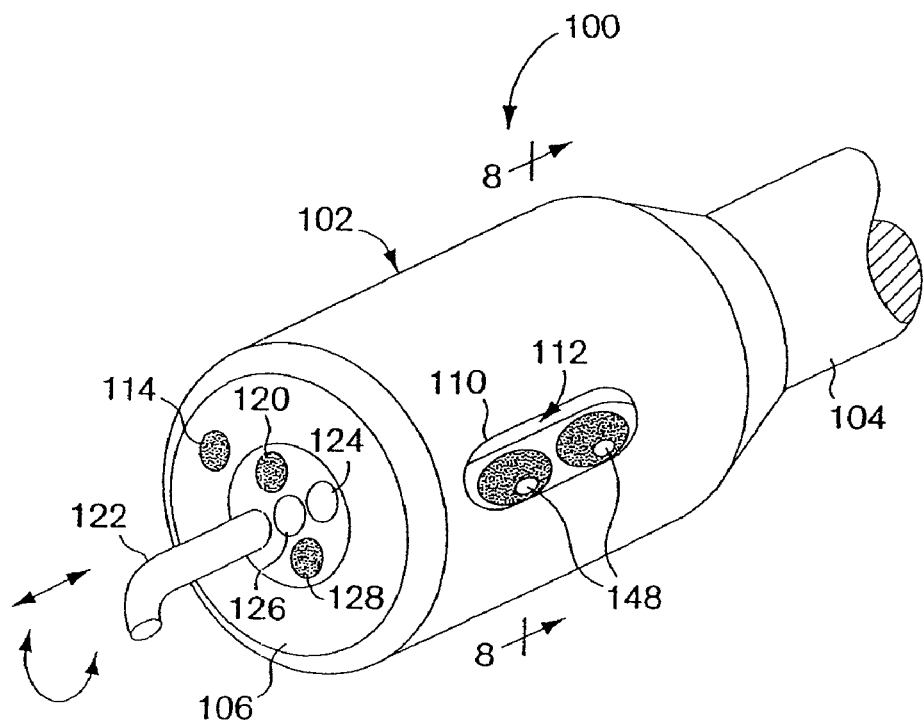
FIG. 6 is an isometric view of an embodiment of the integrated endoscope and medical device treatment accessory comprising a cylindrical cartridge assembled over the distal end of the endoscope.
Figure 7:
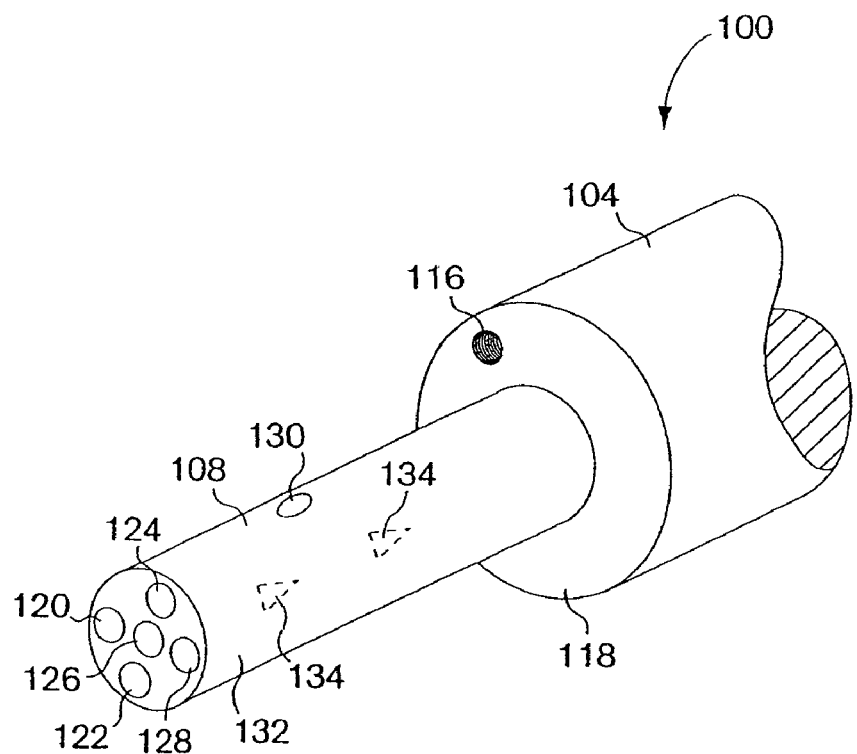
FIG. 7 is an isometric view of an embodiment of the integrated endoscope and medical device treatment accessory wherein the cylindrical cartridge has been removed from the distal end of the endoscope.

FIG. 6 shows another embodiment of an integrated endoscope 100 having a tissue apposition device 102 at its distal end 104. The tissue apposition portion 102 comprises a removable cylindrical cartridge 106 that is received over a reduced diameter core section 108 of the endoscope, shown in FIG. 7. The cylindrical cartridge defines a suction port 110 and vacuum chamber 112 into which a tissue portion may be collected under vacuum. The cartridge also holds tissue capturing means that are delivered into the tissue along a circumferential path relative to the longitudinal axis of the endoscope. The cartridge may be preloaded with the tissue capture means and may be made as a one-time use item that is disposable after use. The cartridge may be secured to the endoscope by a screw 114 threaded into screw hole 116 on a distal face 118 of the endoscope prior to its reduction to the reduced diameter portion 108.

Through the reduced diameter core portion 108 extend passages for conventional endoscope elements. A combination suction lumen and working channel 120 is provided to carry elongated medical instruments. A telescoping and rotational objective lens 122 is provided as well as a fixed objective lens 124 for providing viewing capability to the proximal end of the endoscope. A light guide 126 may be provided at the center of the reduced diameter portion 108 to illuminate areas viewed through the objective lenses. An air and water port 128 may be provided as a cleaning means for the objective lenses. Also provided is a side suction port 130 on the side wall of the reduced diameter portion 108 for communicating vacuum to the vacuum chamber 112 of the cylindrical cartridge. Also provided on the side wall 132 of the reduced diameter portion 108 are dual trigger mechanisms 134 (shown in phantom) that slide longitudinally to operate the tissue capture means release mechanism in the cylindrical cartridge.

Figure 8:
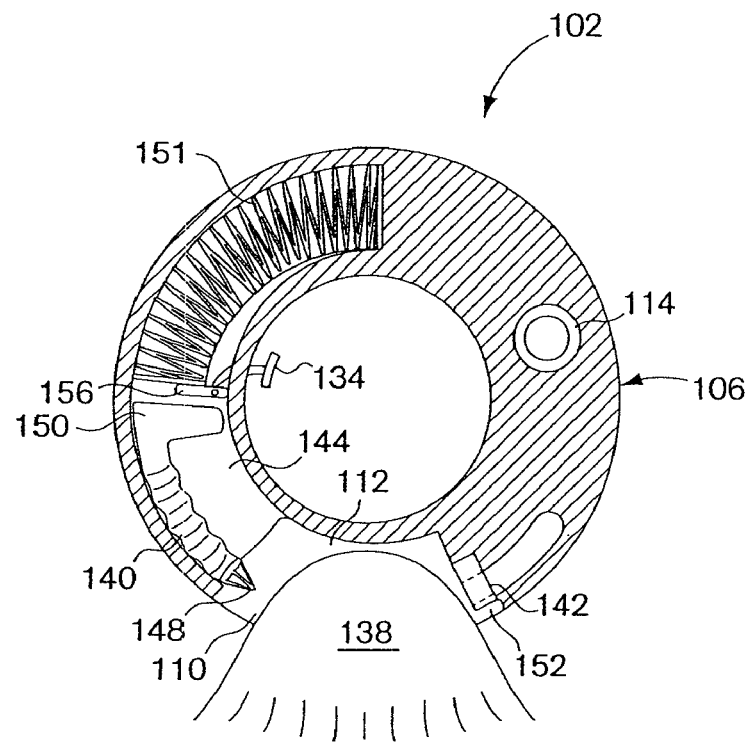
FIG. 8 is a sectional view of the integrated endoscope shown in FIG. 6 taken along the line 8-8.
Figure 9:
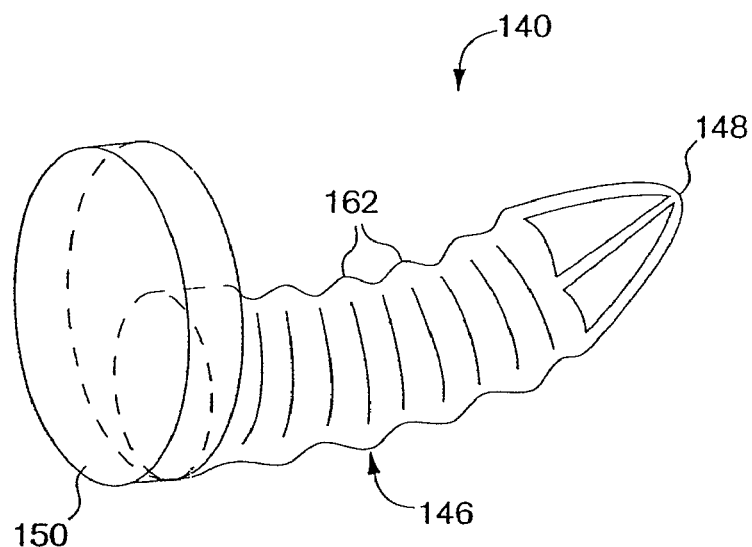
FIG. 9 is a side view of the plug portion of a tissue apposition means device.
Figure 10A:
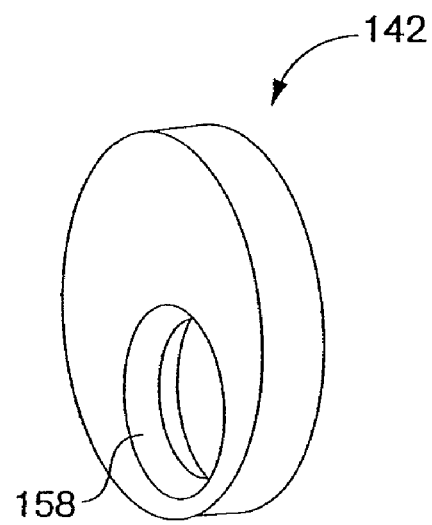
FIGS. 10A and 10B are views of the ring portion of a tissue apposition means.
Figure 10B:
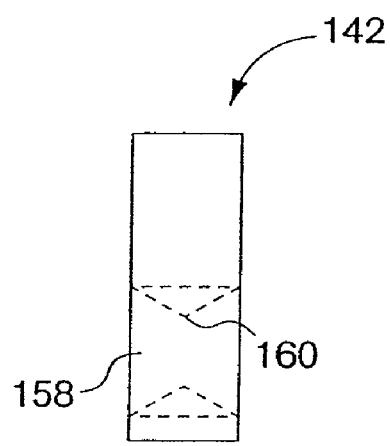

The specific structure of the cylindrical cartridge 106 is shown in the sectional view presented in FIG. 8, taken along the line 8-8 of FIG. 6. In FIG. 8, a tissue portion 138 is shown aspirated and collected into vacuum chamber 112 through suction port 110 of the cartridge. A single mound of tissue 138 may be collected or two separate mounds collected if a partition is placed midway along the length of the suction port 110 to define two separate mounds of tissue. The cartridge carries two sets of tissue apposition means comprising a plug 140 insertable through the tissue and engaging with a fastening ring 142 on the through side of the tissue. A detail of the plug is shown in FIG. 9. Details of the ring are shown in FIGS. 10A and 10B.

The plug is pre-loaded and retained in a circumferential firing chamber 144 defined in the annular cross section of the cylindrical cartridge 106. The plug is curved to follow the arc shape of the firing chamber 144. The plug has a sharp piercing end 148 to penetrate tissue and a flat enlarged diameter cap portion 150 that is engaged by a firing spring 151 to drive the plug circumferentially through the captured tissue 138 and into the ring 142 frictionally held in a ring receptacle 152 formed in the cartridge 106. Because the plug 140 travels along the outside wall 144 of the firing chamber during its travel, the enlarged flat head 150 is offset from the center of the plug body to fully capture the driving force of firing spring 151 and to keep the plug 140 aligned within the firing chamber 144 as it is advanced.

The firing spring 151 is held in a compressed configuration by trigger 156 until delivery of the plug through a captured tissue portion as desired. The trigger can be pulled out of the way from the spring by a remote connection to the proximal end of the endoscope as will be explained below. When the spring is released, it expands along the circumferential pathway as defined by the firing chamber 144 and pushes the plug 140 through the tissue. As the plug is fired, the plug body 146 becomes frictionally engaged in ring through hole 158. Shown best in FIGS. 10A and 10B, the ring through hole is not concentric with the outside diameter of the ring, but is located at one side of the ring to match the alignment of the offset plug body 146 relative to the plug head 150. Additionally, the through hole 158 is configured to taper gradually in diameter to a ridge 160 of reduced diameter in its center for the purpose of enhancing frictional engagement with the plug body 146.

The plug body 146 is made of a series of larger diameter ribs 162 that further enhance frictional engagement with the ring as they meet peaks of resistance as they align with the ridge 160 of the through hole 158 in the ring. As mentioned above, the cartridge 106 may be configured to hold two or more ring and plug assemblies spaced apart longitudinally by approximately one centimeter so that the tissue portion is secured simultaneously by two ring and plug assemblies. If a dividing wall is placed in the suction port 110, dividing it in half longitudinally, then two separate tissue mounds are formed and captured separately by the two ring and plug assemblies.

Figure 11:
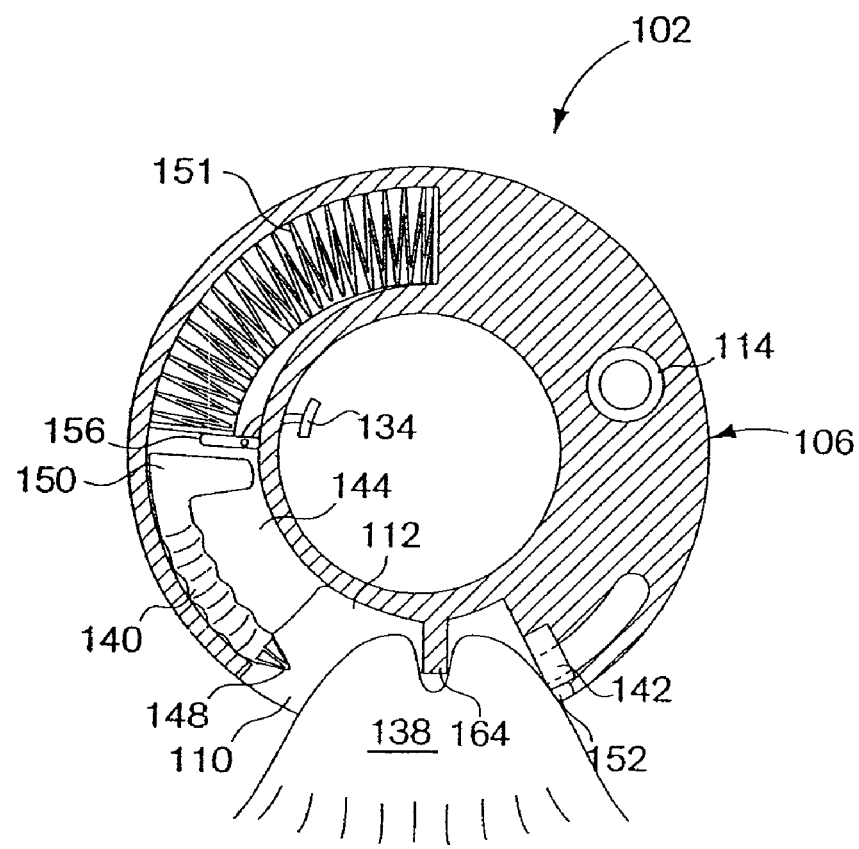
FIG. 11 is a sectional view of an alternate embodiment of the cylindrical cartridge shown in FIG. 6, taken along the line 8-8.
Figure 12:
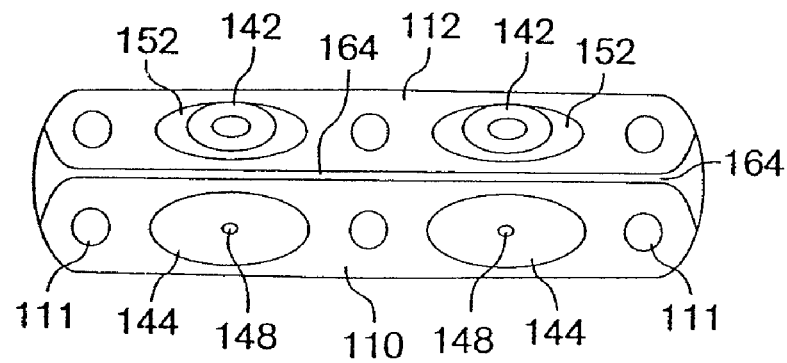
FIG. 12 is a top view of the suction port of the cylindrical cartridge shown in FIG. 11.

In an alternate arrangement, the suction port 110 may be divided by a partition wall extending longitudinally, as shown in FIGS. 11-14. As shown in FIGS. 11 and 12, the cylindrical cartridge 106 may be provided with a suction port 110 having a partition wall 164 extending longitudinally along its length.

Figure 13:
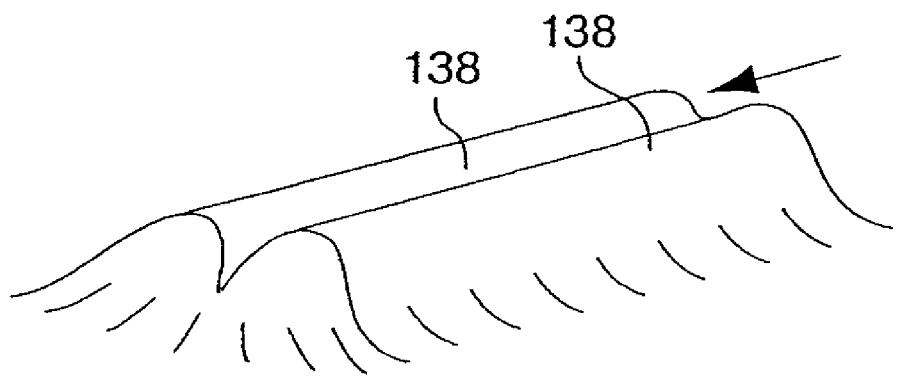
FIG. 13 is a diagrammatic illustration of two tissue portions after being aspirated into the suction port shown in FIG. 12.

When the tissue portion is aspirated into the vacuum chamber 112, it is partitioned around the wall 164 to form two distinct mounds 138 as shown in FIGS. 11 and 13.

As shown in FIG. 12, the partition wall 164 extends across the suction port 110. The overhead view of the suction port 100 as shown in FIG. 12 demonstrates that vacuum is introduced into the vacuum chamber through suction holes 111 spaced throughout the vacuum chamber 112. Firing chambers 144 located at the bottom of the suction chamber, are arranged to aim the sharp piercing tip 148 of the pre-loaded plugs outward into tissue along a circular path so that they curve around through the two mounds of tissue segregated by the partition wall 164 and enter the rings 142 frictionally held in ring retainers 152 positioned on the opposite side of the vacuum chamber 112.

Figure 14:
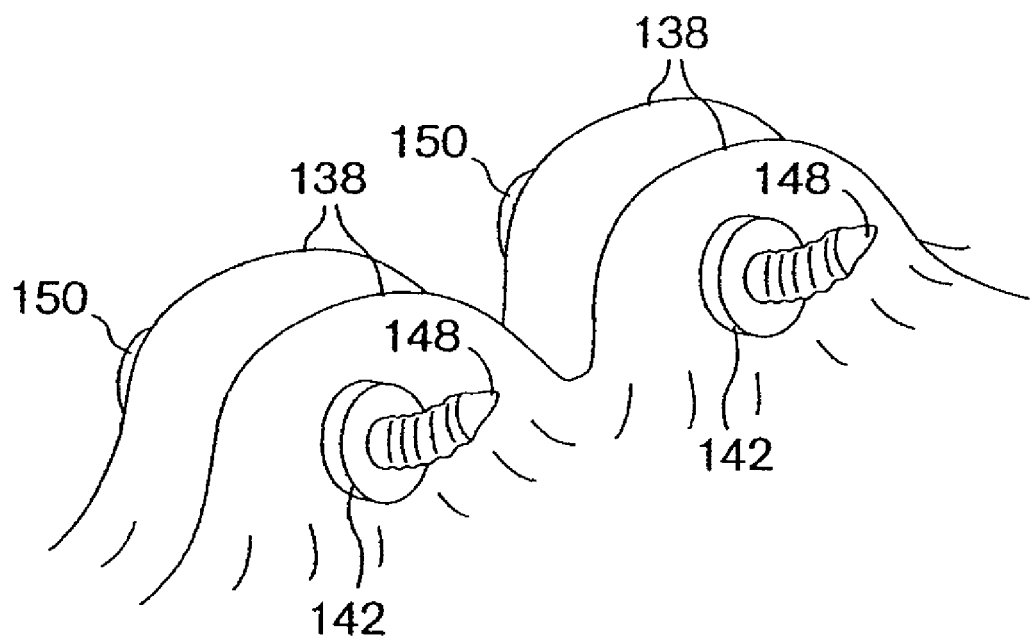
FIG. 14 is an illustration of tissue portions secured together by the apposition device shown in FIGS. 9-10B.
Figure 15:
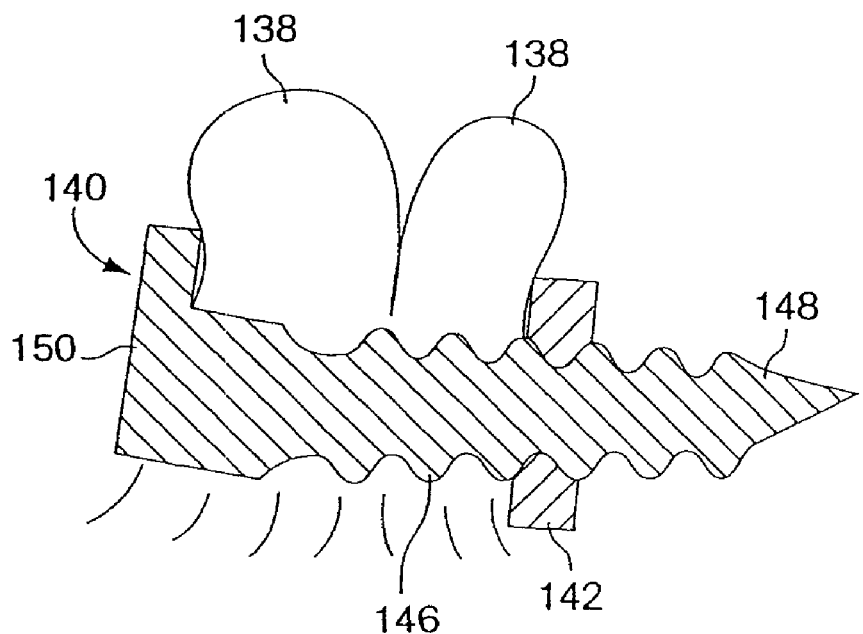
FIG. 15 is a side sectional view of tissue portions captured together by the tissue apposition device of FIGS. 9-10B.
Figure 16:
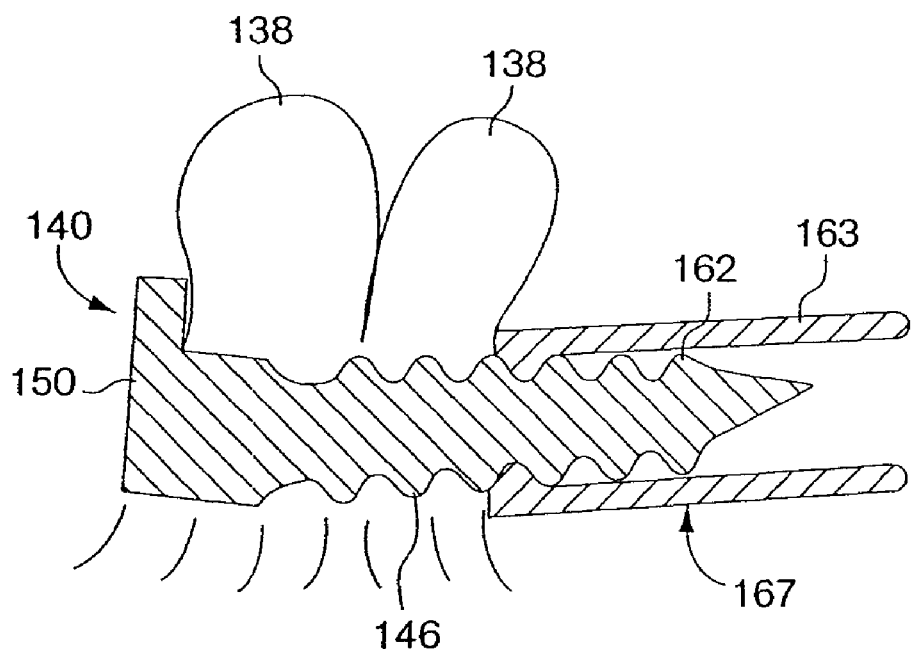
FIG. 16 is a side sectional view of tissue portions captured together by a modified version of the tissue apposition device shown in FIGS. 9-10B.

After the plugs 140 have been driven through the tissue and engaged with the rings 142 on the opposite side of the vacuum chamber, aspiration is discontinued and the tissue mounds 138 captured by the plug and ring 140 and 142 appear as shown in FIGS. 14 and 15. The plug 140 is inserted through both mounds of the partitioned tissue 138 and holds the tissue together in separate mounds with large cap 150 bearing on one side of the tissue and the ring 142 bearing on the other side of the tissue and locked onto the tip of the plug 140. In FIG. 16 is shown an alternate embodiment of a ring 162. The ring performs in the same manner as ring 142 but includes an extended cylindrical portion 164 that extends over the protruding sharp distal tip 148 of the plug so that adjacent tissue areas are not injured by the piercing tip.

Figure 17:
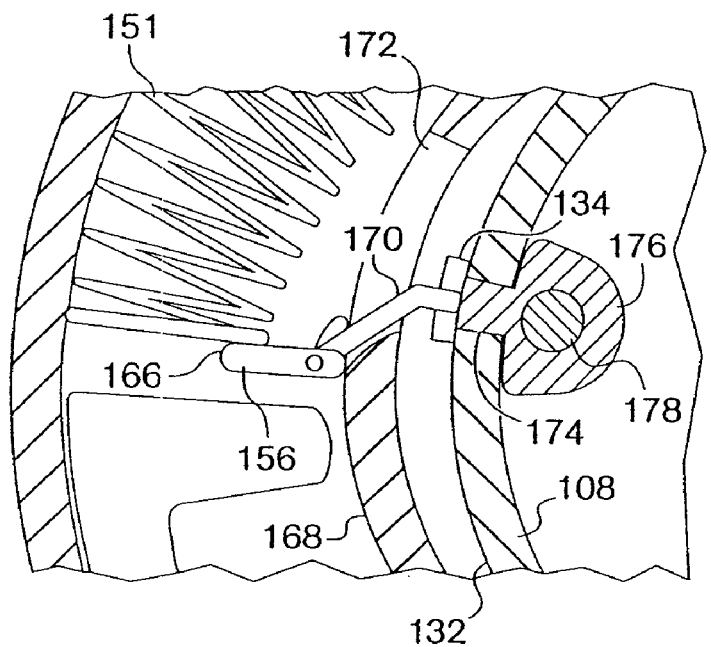
FIG. 17 is a detailed view of the trigger mechanism of the cylindrical cartridge shown in FIG. 6.
Figure 17A:
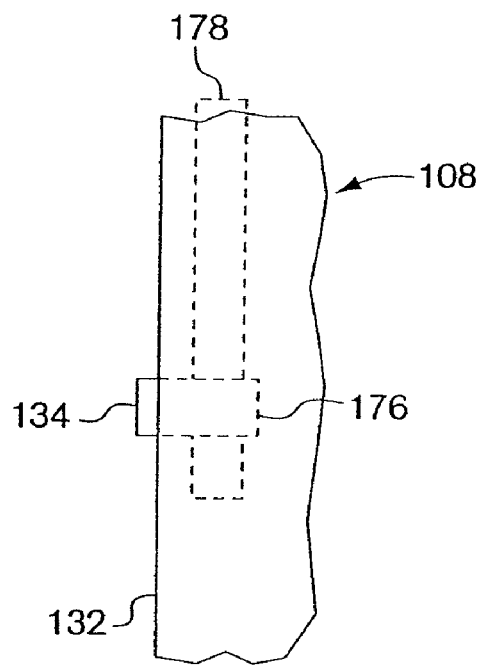
FIG. 17A is a top view of a portion of the reduced diameter portion of the integrated endoscope shown in FIG. 7.
Figure 18:
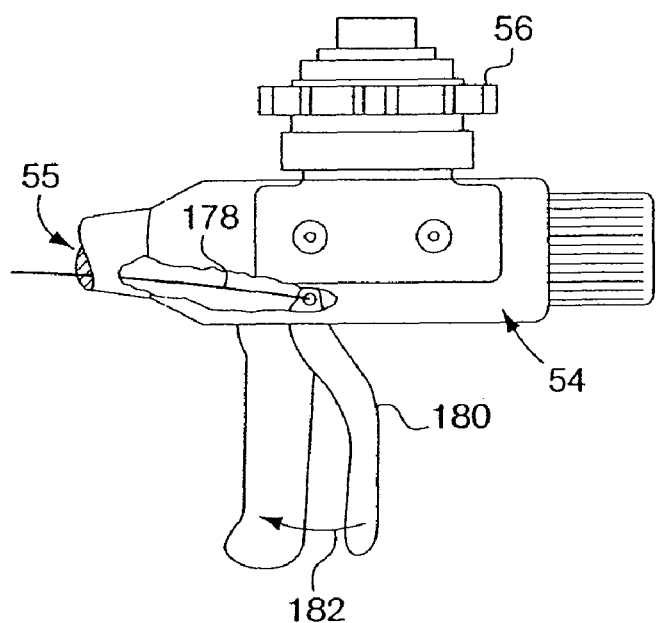
FIG. 18 is a top view of an endoscope control handle employing a trigger lever.

FIG. 17 shows a detailed drawing of the trigger 156 and trigger mechanism 134 that selectively releases the firing spring 151 to deliver the plug into the ring. The trigger 156 comprises a spring engaging portion 166 that is slidably engaged with the inner side wall 168 of the cartridge 106. The spring engaging portion is pinned to a curved portion 170 of the trigger that extends through a trigger slot 172 and engages the trigger mechanism 134 that is slidably positioned on the exterior surface 132 of the reduced diameter portion 108 of the endoscope. The trigger mechanism 134 extends through a slot 174 formed through the wall of reduced diameter portion 108 and forms an eyelet portion 176 that receives a trigger cable 178 that extends through the length of the endoscope shaft 53 to the handle 89 where it is joined to the working end of a trigger lever 180 that extends to the exterior of the handle for activation by the user as shown in FIG. 18. When the lever is operated as shown by arrow 182 in FIG. 18, the trigger cable 178 is pulled proximally, which serves to slide trigger mechanisms 134 proximally as shown in the top view—FIG. 17A). Movement of the trigger mechanism 134 proximally pulls the curved portion 170 and entire trigger 156 proximally such that the spring engaging portion 166 is pulled clear of the firing spring 151, allowing it to release and fire the plug along its circumferential path in the firing chamber 144.

Figure 19:
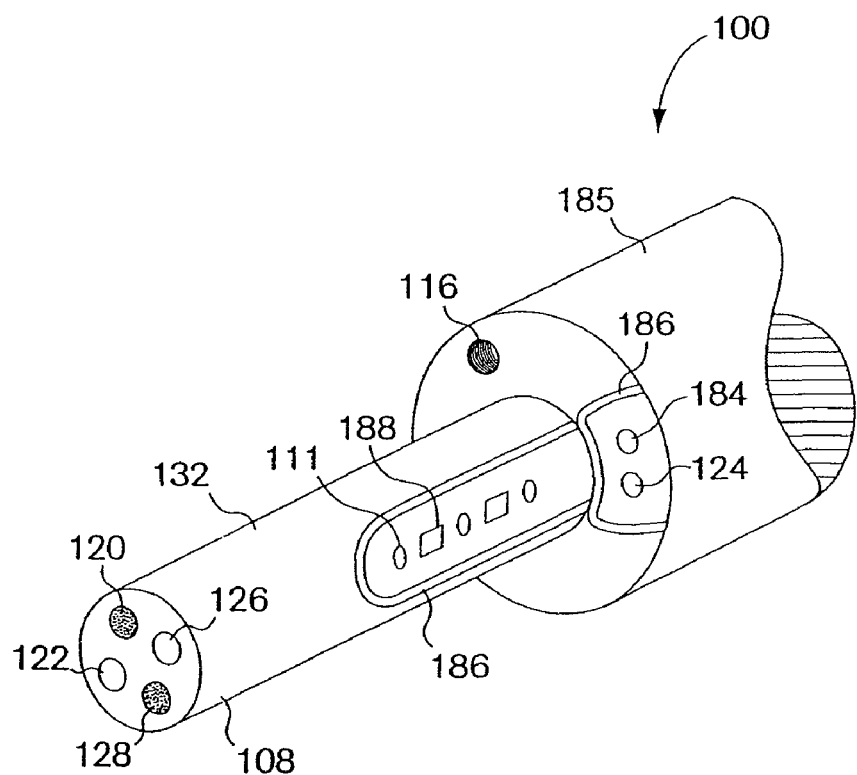
FIG. 19 is a variation of the cylindrical cartridge integrated endoscope embodiment employing a modified reduced diameter portion.

In FIG. 19 is shown an alternate embodiment of the cylindrical cartridge apposition device. The modified endoscope 185 has a reduced diameter portion 108 for receiving the cylindrical cartridge 106 as with the previous embodiment discussed in connection with FIGS. 6 and 7; however, the endoscope further includes a viewing lens 124 and light source 184 on the large diameter end face 118 to provide additional viewing capability. Specifically, the additional viewing lens and light source will permit the operator to directly view tissue being suctioned into the vacuum chamber 112 of the cylindrical cartridge (not shown in FIG. 19). The vacuum chamber of the cylindrical cartridge may have additional cutouts to eliminate walls that would otherwise obstruct the viewing capability of the lens 124. Accordingly, sealing gaskets 186 are employed around the areas that will be overlayed by the vacuum chamber 112 when the cartridge is fitted over the reduced diameter portion 108 of the endoscope. The gaskets will help to ensure a sufficient vacuum is generated in the vacuum chamber to aspirate tissue completely before firing of the plug and ring tissue apposition elements.

Additionally, sensors 188 may be placed adjacent to suction holes 111 on the side wall surface 132 of the reduced diameter portion 108 that signal when tissue has been fully aspirated into the vacuum chamber of the cartridge and send an electrical signal to the proximal end of the endoscope that can notify the user that sufficient aspiration has been obtained and firing of the tissue capture means can be commenced.

Figure 20:
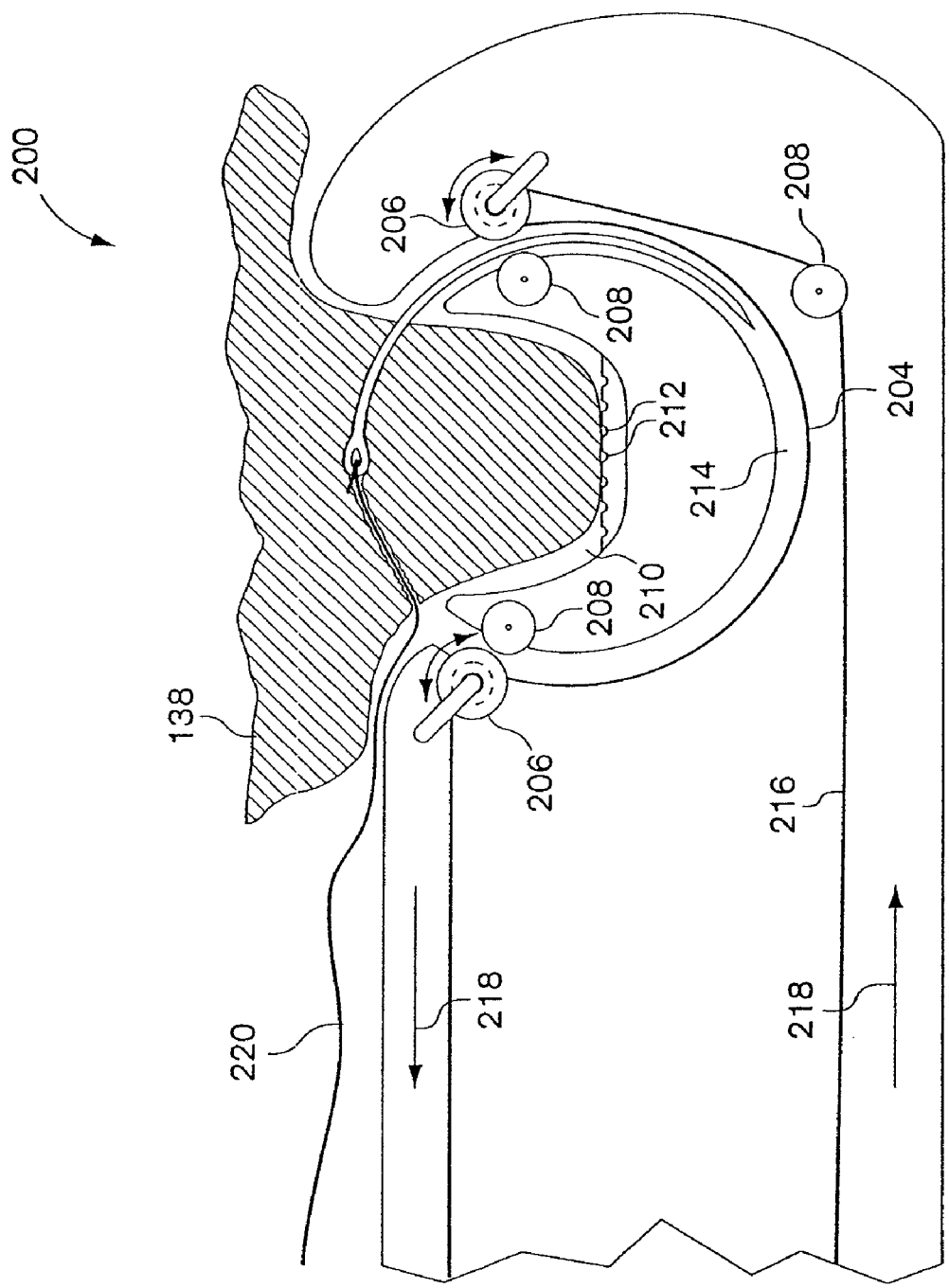
FIG. 20 is a sectional side view of an integrated endoscope and accessory applying a semicircular needle for placing sutures through captured tissue portions.

FIG. 20 shows another embodiment of a tissue apposition device that may be embodied at the distal end of an integrated endoscope. The apposition device 200 employs a semicircular needle 202 driven through a circular pathway 204 that is defined by two pairs of opposed pulleys 206 and 208. The circular pathway 204 guides the needle through a vacuum chamber 210 which captures a tissue portion 138 by aspiration when vacuum is introduced through vacuum holes 212 at the bottom of the suction chamber.

As mentioned above, the needle 202 travels through a circular pathway 204 defined by two sets of pulleys 206 and 208 and a circular needle track 214 that is formed at the distal end of the device 200 such that at least a portion of its arc travels through the vacuum chamber 210 so that the needle will pass through the tissue. Needle track 214 is a circular passage of a diameter slightly greater than that of the needle to guide the needle as it is driven by pulleys. The sets of opposing pulleys each comprise a driver pulley 206 and an idler pulley 208 that is opposed to the driver pulley. To drive the needle, the driver pulleys are adjusted to move slightly into the needle track 214, closing the distance with the idler pulley so that the needle 202 becomes trapped therebetween. When the driver pulleys 206 are rotated, their engagement with the needle will cause the needle to move through the needle track 214 to complete a circular cycle. The driver pulleys may be moved into an out of engagement by mechanical linkage controlled at the proximal end of the endoscope (not shown).

The driver pulleys 206 are driven by a driver cable 216 threaded around each pulley and around an idler pulley 208 and extending proximally through the endoscope to be driven by an external source. When moved in the direction designated by arrows 218, the needle will be driven in a penetrating direction to deliver attached suture thread 220 through a tissue portion 138. After the needle has been passed through the tissue portion 138, vacuum may be discontinued to release the tissue portion and the distal tip of the endoscope moved to a new location, tissue aspirated and the needle again moved through its circular path to deliver the same suture lead. After placing sutures through the desired number of tissue locations, the device may be withdrawn carrying the threaded suture 220 proximally outside of the patient where knots may be applied or suture lock devices assembled onto the suture to secure it and complete the procedure.

Figure 21:
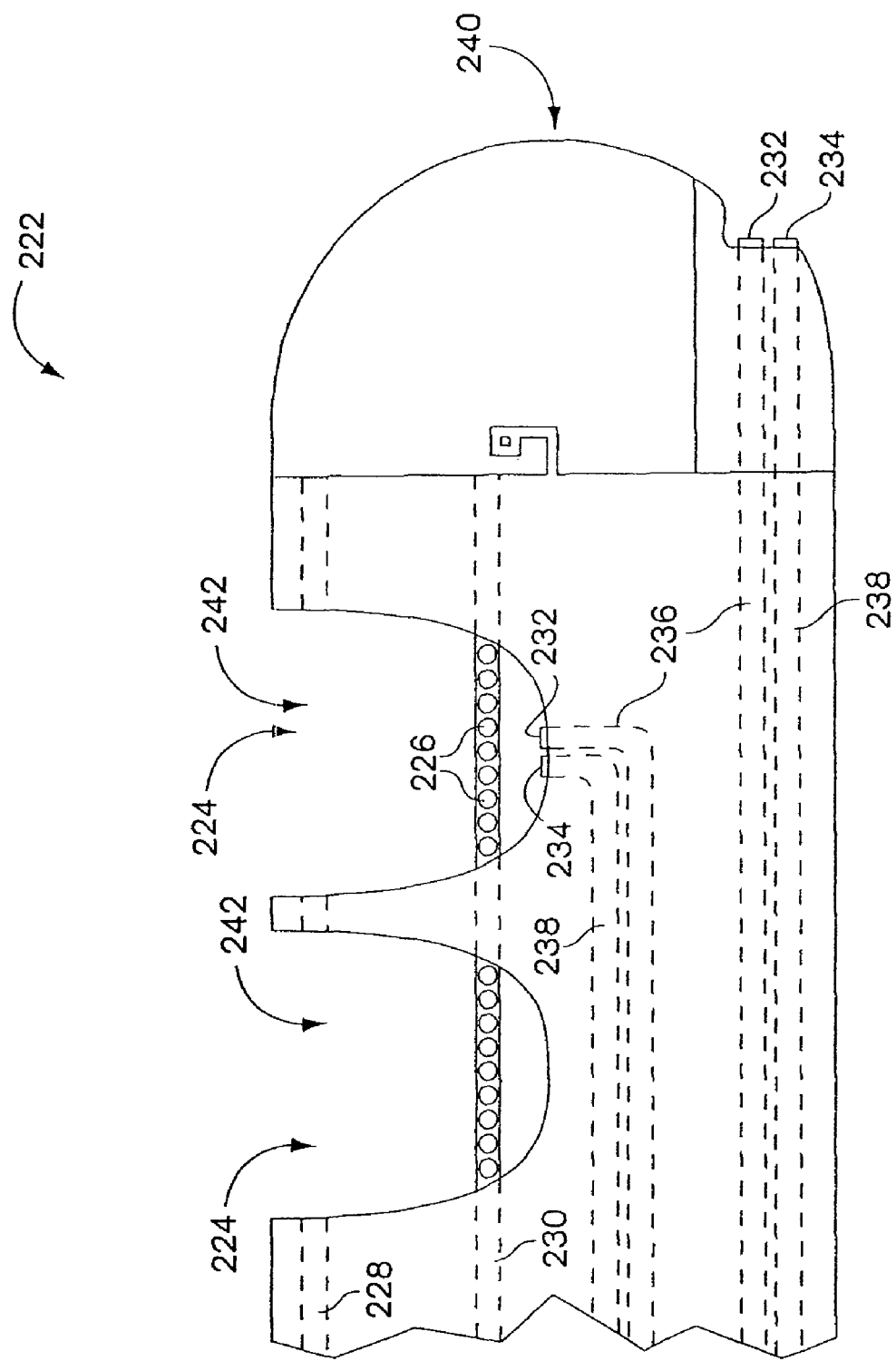
FIG. 21 is a side view of an integrated endoscope employing additional optics and optic cleaning ports.

FIG. 21 shows another embodiment of the multiple suction port tissue apposition device shown in FIGS. 4A-4D. In particular, FIG. 21 shows an integrated endoscope 222 having multiple suction chambers 224 into which tissue may be aspirated by introduction of vacuum through vacuum holes 226. In addition to the working channel lumen 228 and vacuum lumen 230, the endoscope is configured with additional viewing ports 232 and complementary adjacent cleaning ports 234. The viewing ports 232 join to a lumen 236 containing an optical fiber extending through to the proximal end of the endoscope and through which viewing capability is obtained. The cleaning ports 234 open to a lumen extending proximally to the proximal end of the endoscope that permit ejection of flushing liquid and air to clean the viewing port lens 232.

The viewing and cleaning ports of the distal tip 240 of the device aid in navigating the endoscope to the intended tissue location by providing a viewing vantage point that is not obstructed by the structure of the apposition device. The viewing and cleaning ports 232 and 234 that terminate in the bottom of the vacuum chamber 242 are useful in observing when the complete tissue mound has been aspirated into the chamber. When a tissue mound is fully collected, it contacts the face of the viewing port 232 causing a "red-out" condition that verifies for the operator that a complete tissue portion has been aspirated and it is safe to deliver the needle carrying a suture through the tissue mound.

Figure 22:
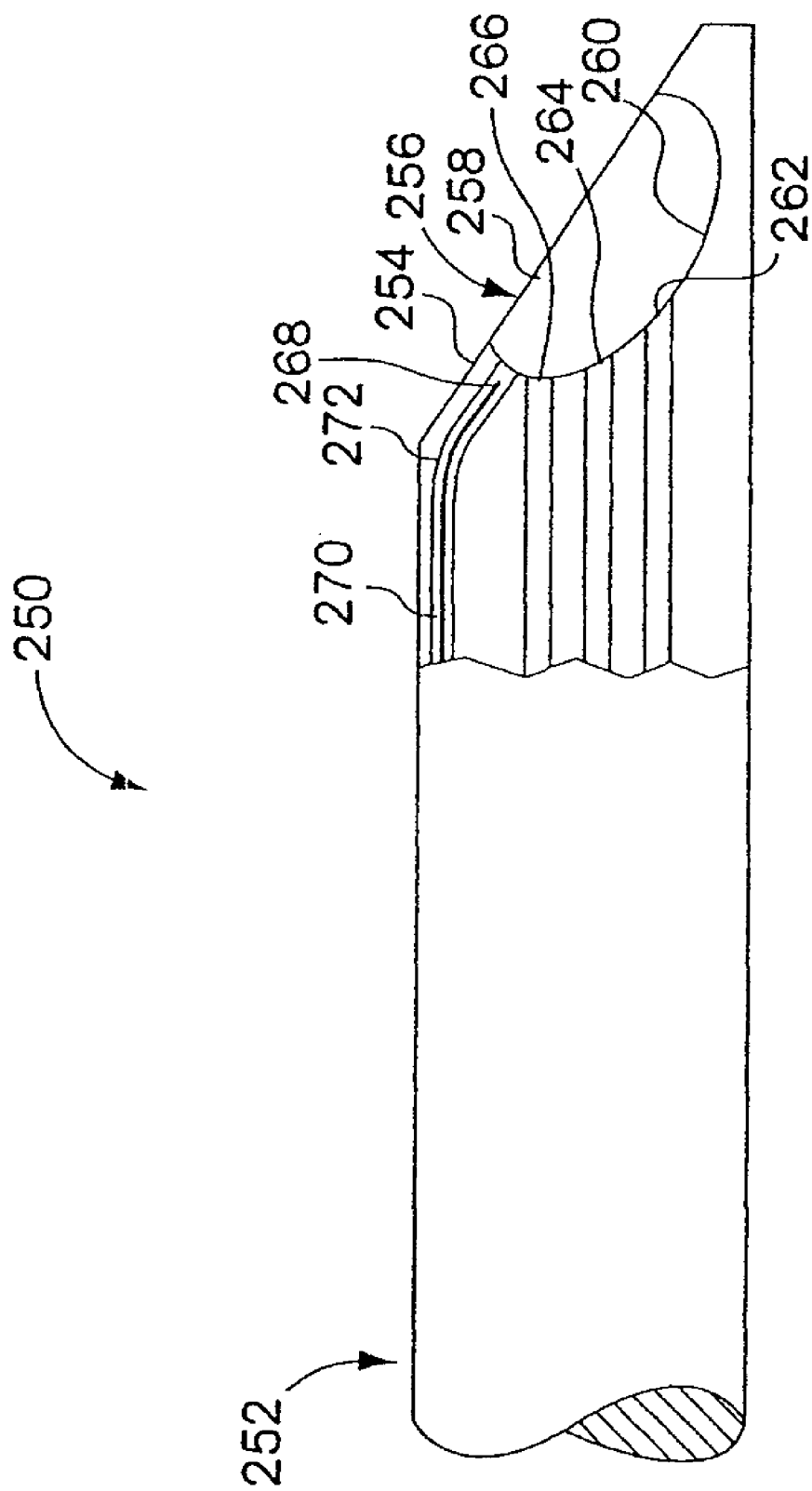
FIG. 22 is a side partial sectional view of an integrated endoscope employing an angulated distal face.

FIG. 22 is a side partial sectional view of another embodiment of the integrated endoscope having a tissue apposition device 250 integrated at its distal end 252. The device utilizes an angulated tip presenting a distal face 254 that is angled away from the longitudinal axis of the endoscope by approximately 45.degree. A suction port 256 is formed on the distal face for receiving tissue aspirated into the vacuum chamber 258. Along the back wall 260 of the vacuum chamber are located several conventional accessory ports found on the endoscopes of other embodiments described in the application.

Specifically, a vacuum port 262 is provided that may be joined to two channels so that either vacuum or pressure for insuflation may be introduced through the same port and into the vacuum chamber 258. Also on the back wall is a viewing lens 264 joined to an optical fiber and an air and water port 266 for cleaning the lens. A rigid needle 268 is directed through a pathway that follows the longitudinal axis of the angulated distal face 54 in order to traverse the vacuum chamber 258 squarely so that captured tissue is accurately penetrated. The needle 268 is advanced by the longitudinal movement of a flexible pusher 270 that is able to traverse the 45.degree. angle corner 272 within an appropriately formed sliding lumen and has sufficient column strength to drive the needle through tissue. The needle may be hollow and deliver a permanent tag through its lumen to secure the tissue with suture as shown in the embodiment of FIGS. 4A and 4C of the prior art devices.

Figure 23:
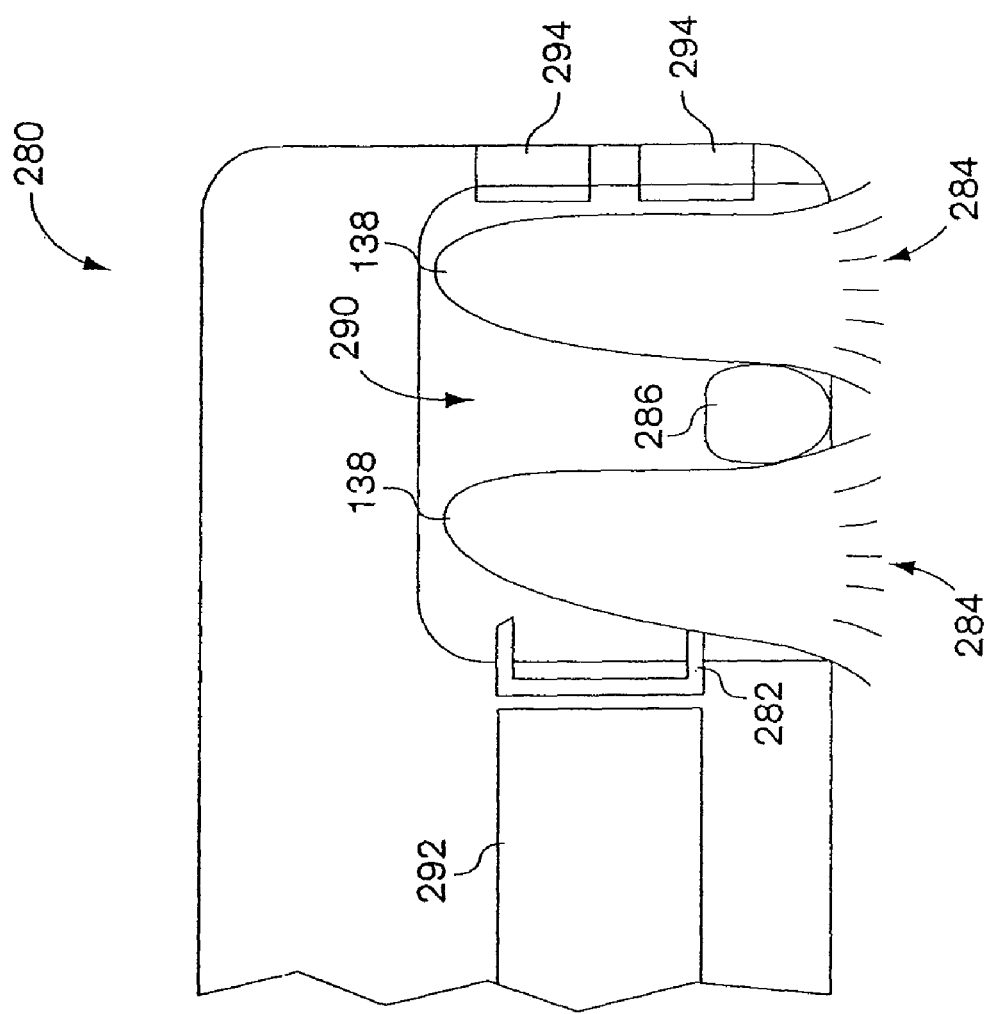
FIG. 23 is a partial sectional side view of an integrated endoscope employing a tissue apposition accessory that deploys staples.
Figure 24:
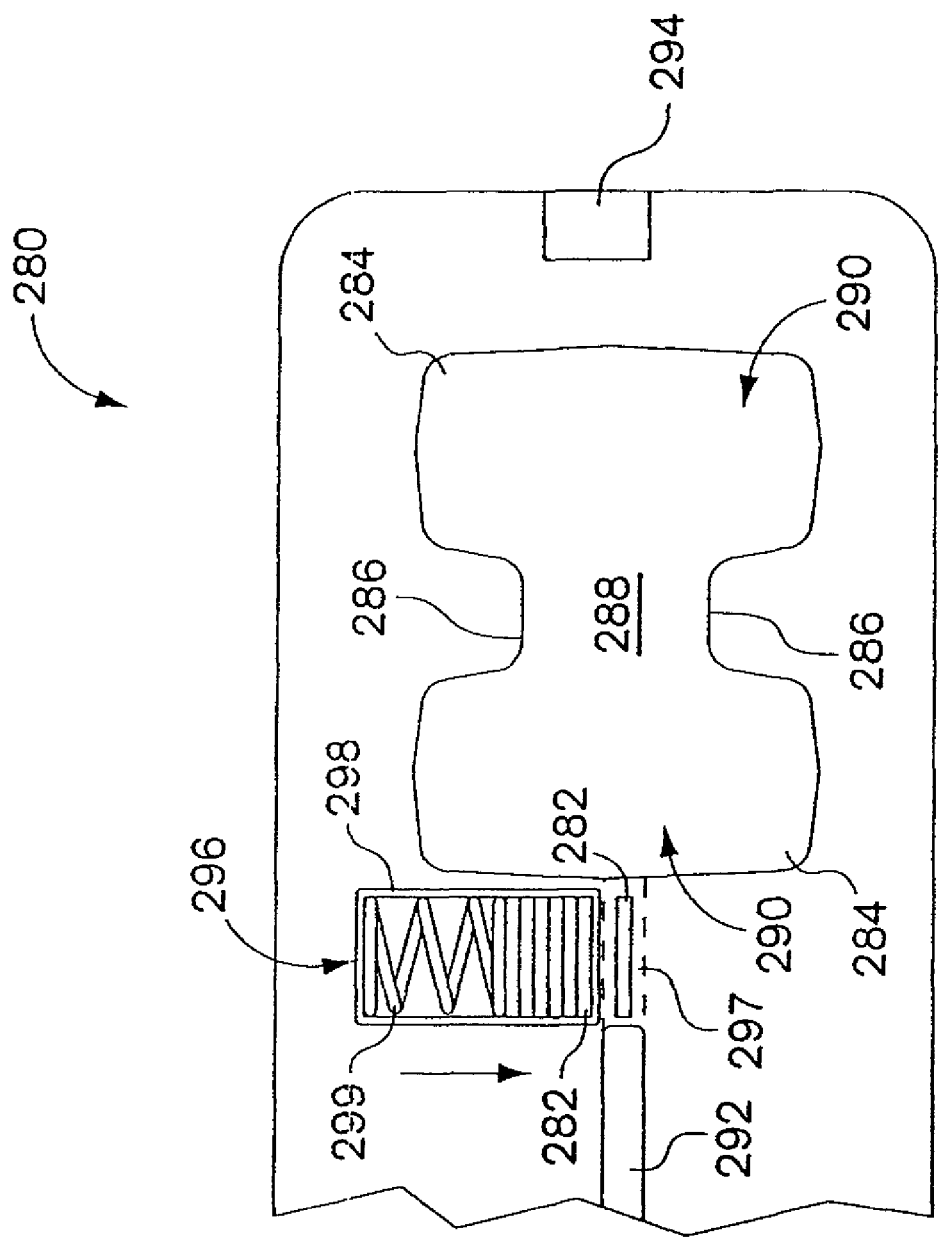
FIG. 24 is a top view of an integrated endoscope employing a tissue apposition device that deploys staples.

FIG. 23 shows another embodiment of the integrated endoscope comprising an apposition device 280 that drives a staple 282 through captured tissue. Multiple tissue mounds are aspirated into dual suction ports 284 separated by a split partition wall 286. Presence of partition wall causes the aspirated tissue to form into two separate mounds around the partition wall 286. As shown in FIG. 24, a gap 288 in the partition wall is provided to allow the stapled tissue portions to be removed from the vacuum chamber 290 without having the staple become caught on the partition wall 286.

In operation, after the tissue mounds are aspirated into the vacuum chamber 290, a staple 282 is advanced distally by pusher rod 292, which may be guided through a working channel of the endoscope. The pusher rod advances distally to cause a staple to penetrate both mounds of tissue 138 and engage anvils 294 that cause the ends of the staple to buckle and collapse to secure the staple in the tissue as a conventional staple performs.

To permit the device to make multiple plications with one intubation, the staple magazine 296 may be provided to advance sequential staples in line with the pusher rod 292 as each preceding staple is ejected. The magazine 296 may comprise a housing 298 with spring 299 keeping a constant force against the supply of staples so that they will eject from the housing automatically as each staple is ejected and the pusher rod 292 returns proximally past the magazine position so that a staple may be ejected into the pusher shaft pathway 297.

Figure 25:
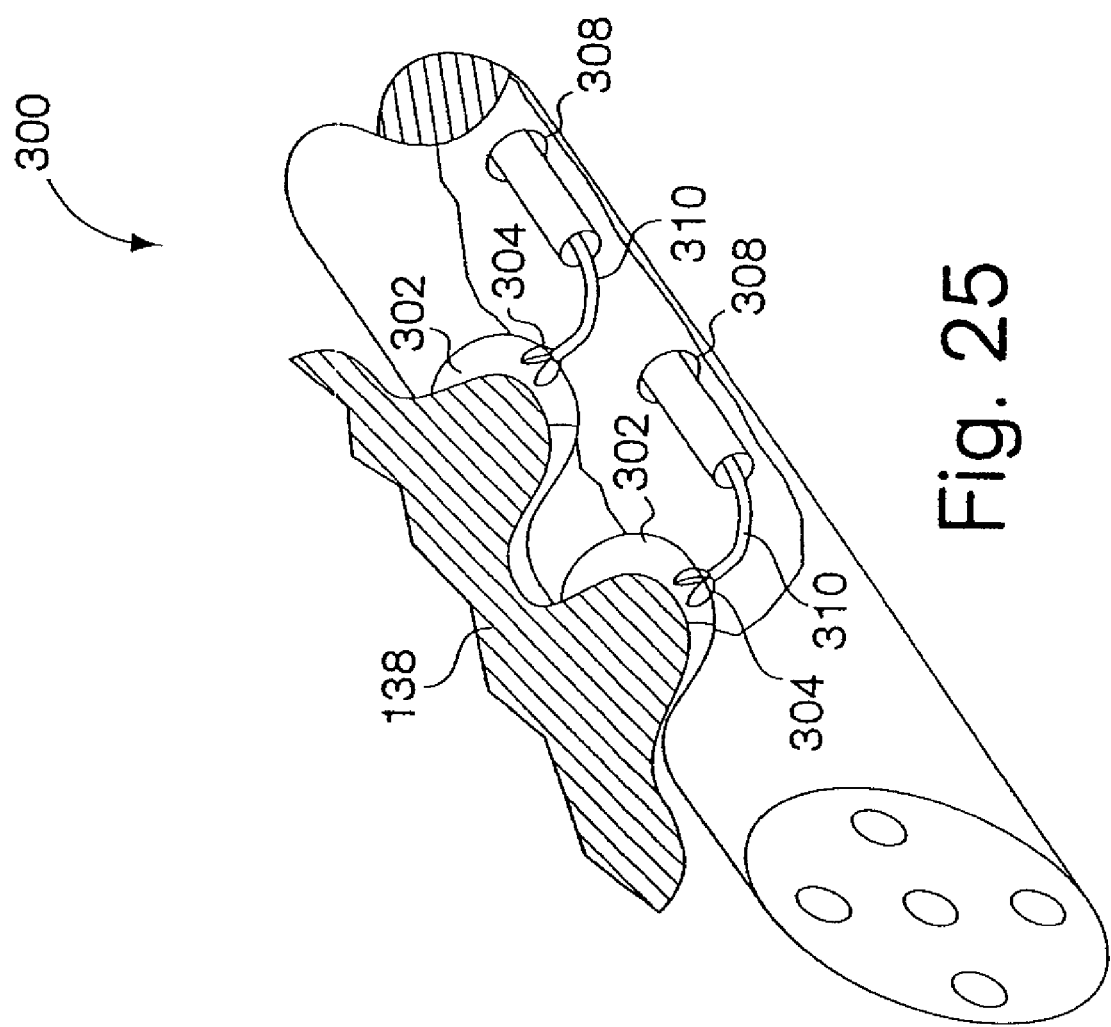
FIG. 25 is an isometric partial sectional view of an integrated endoscope and accessory employing multiple access ports.

FIG. 25 shows another embodiment of the integrated endoscope/accessory concept providing an apposition device 300 having multiple access ports 302 through which tissue can be grasped and manipulated. Tissue may be grasped through the ports 302 by means such as forceps 304 as shown in FIG. 25. The forceps 304 may be advanced through working channels 308 and bend upward at articulation points 310 to extend through the access ports 302 to grasp tissue portions 138. As the forceps are withdrawn back through the access ports 302, the tissue mounds form as they engage the sides of the ports and are pulled in to the device.

Once grasped, the tissue mounds 138 may be injected with a bio absorbable bulking agent by a needle introduced through another channel of the endoscope. Alternatively, the tissue mounds may be retained by placement of a ligating band on each tissue mound. The tissue mounds may be grasped through the access ports by other means such as a barbed harpoon, a snare loop or rollers.

Figure 26:
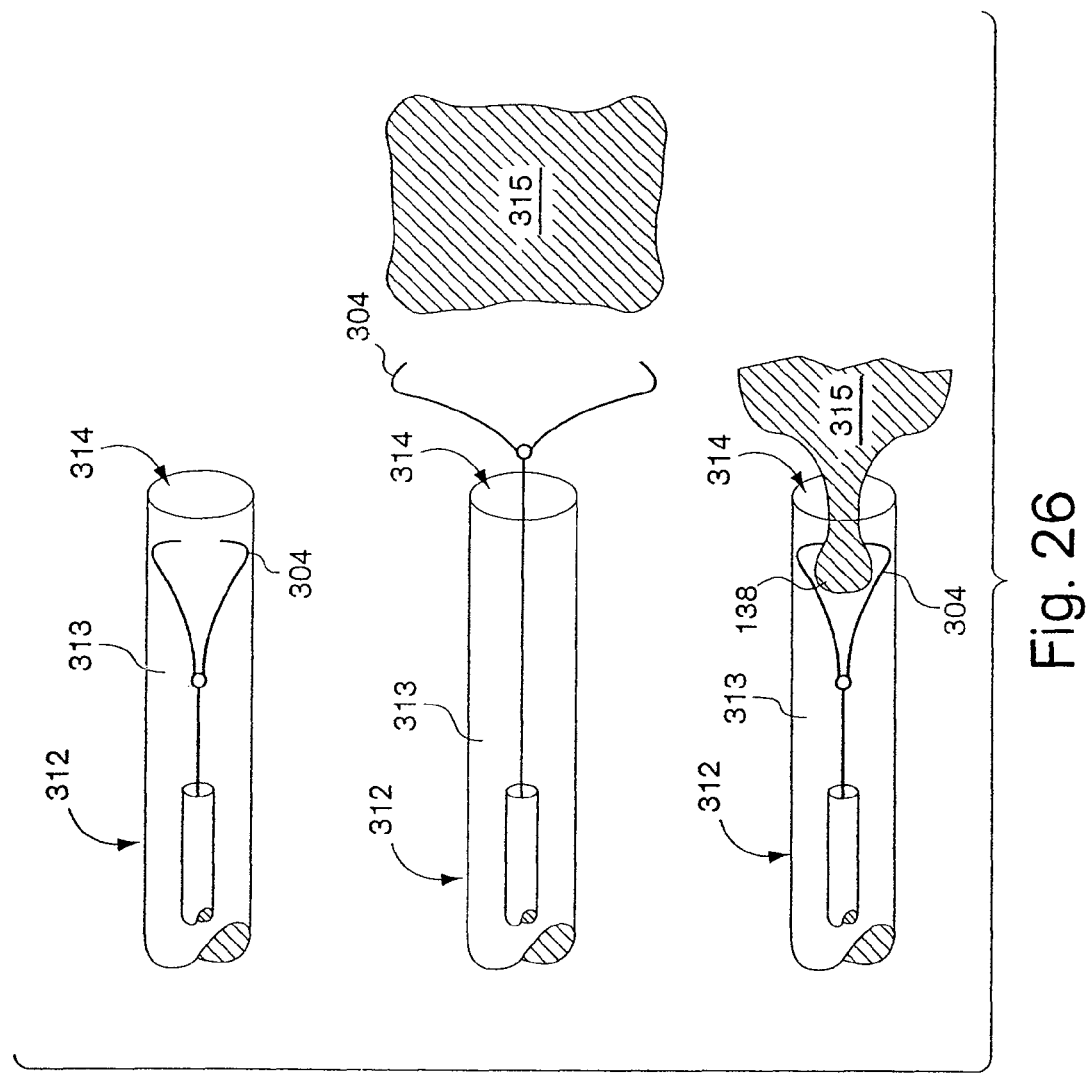
FIG. 26 is a series of three views of an integrated endoscope with a single access port and grasping device in various stages of operation.

As shown in FIG. 26, the grasping mechanisms may be employed through an open distal end of an endoscope embodiment 312 providing a single access port 314. FIG. 26 shows a progression of steps in which a grasping device such as a forceps 304 is first navigated within the open chamber 313 at the distal end of the endoscope 312 and guided to a tissue location 315. When the desired tissue location is reached, the forceps 304 is advanced from the open chamber 313 and expanded to grasp a tissue portion. Once the tissue portion is grasped, the forceps are closed to pull it into the open chamber 313 of the endoscope 312 to define a tissue mound 138 that can then be manipulated with a tissue securing device.

It should be understood however, that the foregoing description of the invention is intended merely to be illustrative thereof and that other modifications, embodiments and equivalents may be apparent to those who are skilled in the art without departing from its spirit. Having thus described the invention what we desire to claim and secure by letters patent is:

The invention claimed is:

1. A method of endoscopically suturing tissue, comprising:
    applying a vacuum to draw tissue to a vacuum chamber of an endoscopic apposition device through a port that opens to the outside of the endoscopic apposition device, the port being located along a side of the endoscopic apposition device between proximal and distal ends of the endoscopic apposition device; and
    driving a needle in the endoscopic apposition device that has an attached suture thread through an arcuate path that passes through the tissue that has been drawn to the vacuum chamber, the arcuate path being located entirely in a single plane extending in an end-to-end direction from the proximal end to the distal end of the endoscopic apposition device.

2. The method of claim 1, wherein the tissue is drawn into the vacuum chamber.

3. The method of claim 1, wherein the needle is driven through a continuous circular path.

4. The method of claim 1, further comprising securing the suture thread after the needle has passed through the tissue.

5. The method of claim 1, wherein the needle is driven in a first direction from an initial position within the endoscopic apposition device and through a complete cycle about the arcuate path back to the initial position.

6. The method of claim 1, wherein the needle is driven through the arcuate path passing through the vacuum chamber.

7. The method of claim 1, wherein the needle is driven through the arcuate path about an axis transverse to the plane that extends in the end-to-end direction.

8. The method of claim 1, wherein the needle is a semicircular needle.

9. The method of claim 1, wherein the endoscopic apposition device includes an arcuate needle track that coincides with a portion of the arcuate path traveled by the needle.

10. The method of claim 9, wherein the arcuate needle track includes a first opening and a second opening into the vacuum chamber.

11. The method of claim 9, wherein the arcuate needle track is located in the plane that extends in the end-to-end direction.

12. The method of claim 9, wherein the needle is driven by a drive system located along the arcuate needle path.

13. The method of claim 12, wherein the endoscopic apposition device is integrated with an endoscope and the drive system is actuated by a control element extending through the endoscope.

14. The method of claim 1, wherein the endoscopic apposition device is integrated with an endoscope and the vacuum chamber communicates with a suction channel of the endoscope.

* * * * *